United States Patent
Cushman et al.

(10) Patent No.: US 9,206,193 B2
(45) Date of Patent: Dec. 8, 2015

(54) SUBSTITUTED NORINDENOISOQUINOLINES, SYNTHESES THEREOF, AND METHODS OF USE

(75) Inventors: Mark S. Cushman, West Lafayette, IN (US); Yunlong Song, Shanghai (CN)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 13/575,505

(22) PCT Filed: Jan. 27, 2011

(86) PCT No.: PCT/US2011/022732
§ 371 (c)(1),
(2), (4) Date: Jul. 26, 2012

(87) PCT Pub. No.: WO2011/094416
PCT Pub. Date: Aug. 4, 2011

(65) Prior Publication Data
US 2012/0302563 A1    Nov. 29, 2012

Related U.S. Application Data

(60) Provisional application No. 61/298,789, filed on Jan. 27, 2010.

(51) Int. Cl.
| | | |
|---|---|---|
| *C07D 471/00* | (2006.01) | |
| *C07D 491/00* | (2006.01) | |
| *C07D 498/00* | (2006.01) | |
| *C07D 513/00* | (2006.01) | |
| *C07D 515/00* | (2006.01) | |
| *A61K 31/44* | (2006.01) | |
| *C07D 493/04* | (2006.01) | |
| *C07D 221/18* | (2006.01) | |
| *C07D 491/04* | (2006.01) | |

(52) U.S. Cl.
CPC ............ *C07D 493/04* (2013.01); *C07D 221/18* (2013.01); *C07D 491/04* (2013.01)

(58) Field of Classification Search
CPC ............................ C07D 221/22; C07D 221/18
See application file for complete search history.

(56) References Cited

U.S. PATENT DOCUMENTS

| | | | |
|---|---|---|---|
| 5,597,831 A | 1/1997 | Michalsky et al. | |
| 5,627,165 A | 5/1997 | Glazier | |
| 6,509,344 B1* | 1/2003 | Cushman et al. ............. | 514/280 |
| 7,312,228 B2 | 12/2007 | Cushman et al. | |
| 7,495,100 B2 | 2/2009 | Cushman et al. | |
| 7,781,445 B2 | 8/2010 | Cushman et al. | |
| 8,053,443 B2 | 11/2011 | Cushman et al. | |
| 2004/0229895 A1 | 11/2004 | Jagtap et al. | |
| 2005/0003502 A1 | 1/2005 | Burgin et al. | |
| 2006/0063736 A1 | 3/2006 | Bertozzi et al. | |
| 2008/0262016 A1 | 10/2008 | Jagtap et al. | |
| 2008/0318995 A1 | 12/2008 | Cushman et al. | |

FOREIGN PATENT DOCUMENTS

| | | |
|---|---|---|
| WO | WO 2000/021537 | 4/2000 |
| WO | WO 2000/034228 | 6/2000 |
| WO | WO 2004/014862 | 2/2004 |
| WO | WO2005/089294 | 9/2005 |
| WO | WO 2005/089294 A2 * | 9/2005 |
| WO | WO 2007/025009 A2 * | 3/2007 |

OTHER PUBLICATIONS

Carey, FA. Organic Chemistry 6th Ed. McGraw Hill. 2006, chapter 1, p. 9.*
Cushman, M. et al. Synthesis and Antitumor Activity of Structural Analogues of the Anticancer Benzophenanthridine Alkaloid Fagaronine Chloride. J. Med. Chem. 1985, vol. 28, p. 1032, compound 4, p. 1033, compound 20, p. 1034, left column, lines 4-8.*
Ulrichova, J. et al. Inhibition of Acetylcholinesterase Activity by some Isoquinoline Alkaloids. Journal of Medicinal Plant Research. 1983, vol. 48, p. 112, compounds 15.*
Gensler, WJ. et al. Synthesis of 11H-Indeno[1,2-c]isoquinoline Compounds Related to Chelerythrine. The Journal of Organic Chemistry. 1968, vol. 33, p. 2862, compound 11d.*
Ulrichova, J. et al. Inhibition of Acetylcholinesterase Activity by some Isoquinoline Alkaloids. Journal of Medicinal Plant Research. 1983, vol. 48, p. 112.*
Gensler, WJ. et al. Synthesis of 11H-Indeno[1,2-c]isoquinoline Compounds Related to Chelerythrine. The Journal of Organic Chemistry. 1968, vol. 33, p. 2862.*
Cushman, M. et al. Synthesis and Antitumor Activity of Structural Analogues of the Anticancer Benzophenanthridine Alkaloid Fagaronine Chloride. J. Med. Chem. 1985, vol. 28, p. 1032.*
Staker et al., "Structures of Three Classes of Anticancer Agents Bound to the Human Topoisomerase I-DNA Covalent Complex," *J. Med. Chem.*, 2005, vol. 48, No. 7, 2336-2345.
Ioanoviciu et al., "Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex as Determined by X-ray Crystallographic Analysis," *J. Med. Chem.*, 2005, vol. 48, No. 15, 4803-4814.
Xiao et al., "On the Binding of Indeno[1,2-c]isoquinolines in the DNA-Topoisomerase I Cleavage Complex," *J. Med. Chem.*, 2005, vol. 48, No. 9, 3231-3238.
Antony et al., "Cellular Topoisomerase I Inhibition and Antiproliferative Activity by MJ-III-65 (NSC 706744), an Indenoisoquinoline Topoisomerase I Poison," *Molecular Pharmacology*, 2005, vol. 67, No. 2, 523-530.
Jayaraman et al., "Synthesis of New Dihydroindeno[1,2-c]isoquinoline and Indenoisoquinolinium Chloride Topoisomerase I Inhibitors Having High In Vivo Anticancer Activity in the Hollow Fiber Animal Model", *J. Med. Chem.*, 2002, vol. 45, pp. 242-249.

(Continued)

*Primary Examiner* — Rita Desai
*Assistant Examiner* — Ben S Michelson
(74) *Attorney, Agent, or Firm* — Mark S. Cohen; Pearl Cohen Zedek Latzer Baratz LLP

(57) ABSTRACT

Described herein are substituted norindenoisoquinoline compounds, and pharmaceutical compositions and formulations comprising the norindenoisoquinoline compounds. Also described herein are methods for using the compounds for the treatment and/or prevention of topoisomerase mediated diseases, such as cancer.

6 Claims, 2 Drawing Sheets

(56) References Cited

OTHER PUBLICATIONS

Staker, B.L.; Hjerrild, K.; Feese, M.D.; Behnke, C.A.; Burgin Jr., A.B.; Stewart, L. "The Mechanism of Topoisomerase I Poisoning by a Camptothecin Analog," *Proc. Natl. Acad. Sci. U.S.A.*, 2002, 99, 15387-15392.
Pommier, Y.; Pourquier, P.; Fan, Y.; Strumberg, D. "Mechanism of Action of Eukaryotic DNA Topoisomerase I and Drugs Targeted to the Enzyme," *Biochim. Biophys. Acta*, 1998, 1400, 83-106.
Kohlhagen, G.; Paull, K.; Cushman, M.; Nagafuji, P.; Pommier, Y., "Protein-Linked DNA Strand Breaks Induced by NSC 314622, a Novel Noncamptothecin Topoisomerase I Poison," *Mol. Pharmacol.*, 1998, 54, 50-58.
Jaxel, C.; Kohn, K. W.; Wani, M. C.; Wa.., M.C.; Pommier, Y., "Structure-Activity Study of the Actions of Camptothecin Derivatives on Mammalian Topoisomerase I: Evidence for a Specific Receptor Site and a Relation to Antitumor Activity," *Cancer. Rev.*, 1989, 49,1465-1469.
Minami, H.; Beijnen, J.H.; Verweij, J.; Ratain, M. J., "Limited Sampling Model for the Area under the Concentration Time Curve of Total Topotecan," *Clin. Cancer Res.*, 1996, 2, 43-46.
Danks, M.K.; Pawlik, C.A.; Whipple, D.O.; Wolverton, J.S., "Intermittant Exposure of Medulloblastoma Cells to Topotecan Produces Growth Inhibition equivalent to Continuous Exposure," *Clinical Cancer Research*, 1997, 3, 1731-1738.
Haas, N.B.; LaCreta, F.P.; Walczak, J.; Hudes, G.R.; Brennan, J.M.; Ozols, R.F.; O'Dwyer, P.J. "Phase 1/Pharmacokinetic Study of Topotecan by 24-Hour Continuous Infusion Weekly," *Cancer Res.*, 1994, 54, 1220-1226.
Shapiro, S.L.; Geiger, K.; Youlus, J.; Freedman, L., "Indandiones. II. A Modified Dieckmann Reaction," *J. Org. Chem.*, 1961, 26,3580-3582.
Pailer, M.; Worther, H.; Meller, A., "Some reactions of 2-aryl-1,3-indandiones," *Monatsh Chem.*, 1961, 92, 1037-1047.
Freireich, E.J., et al., "Quantitative Comparison to Toxicity of Anticancer Agents in Mouse, Rat, Hamster, Dog, Monkey, and Man," *Cancer Chemother. Rep.*, 1966, 50 (4), 219-244.
Nagarajan, M.; Xiao, X.; Antony, S.; Kohlhagen, G.; Pommier, Y.; Cushman, M., "Design, Synthesis, and Biological Evaluation of Indenoisoquinoline Topoisomerase I Inhibitors Featuring Polyamine Side Chains on the Lactam Nitrogen," *J. Med. Chem,.* 2003, 46, 5712-5724.
Hollingshead, M.; Plowman, J.; Alley, M.; Mayo, J.; Sausville, E., "The Hollow Fiber Assay," *Contrib. Oncol,.* 1999, 54, 109-120.
Plowman, J.; Camalier, R.; Alley, M.; Sausville, E.; Schepartz, S., "US NCI Testing Procedures," *Contrib. Onco,l.* 1999, 54, 121-135.
Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.*, 2003, 63, 7428-7435.
West, Anthony R., "Solid State Chemistry and its Applications," Wiley, New York, 1988, pp. 358 & 365.
Kucerova, T., et al., "Solovolysis of O-acyl-10-hydroxy-10-dihydro-indeno[1,2-c]Isoquinolin—5,11-diones," 1979, Database CA, Chemical Abstracts Service, Database Accession No. 1980:22814.
Cushman, Mark, et al.,"Synthesis of a New Indeno[1,2-c]Isoquinolines: Cytotoxic Non-Camptothecin Topoisomerase I Inhibitors," 2000, *Journal of Medicinal Chemistry*, vol. 43, No. 20, pp. 3688-3698.
Jayaraman, Muthusamy, et al., "Synthesis of New Dihydroindeno[1-2-*c*]Isoquinolone and Indenoisoquinolinium Chloride Topoisomerase I Inhibitors Having High In Vivo Anticancer Activity in the Hollow Fiber Animal Model," 2002, *Journal of Medicinal Chemistry*, vol. 45, No. 1, pp. 242-249.
Morrell, Andrew, et al., "Synthesis, of Nitrated Indenoisoquinolines as Topoisomerase I Inhibitors," 2004, *Bioorganic & Medicinal Chemistry Letters*, vol. 14, pp. 3659-3663.
Nagarajan, Muthukaman, et al., "Synthesis and Anticancer Activity of Simplified Indenoisoquinoline Topoisomerase I Inhibitors Lacking Substituents on The Aromatic Ring," 2004, *Journal of Medicinal Chemistry*, vol. 47, No. 23, pp. 5651-5661.

Strumberg, Dirk, et al., "Synthesis of Cytotoxic Indenoisoquinoline Topoisomerase I Poisons," 1999, *Journal of Medicinal Chemistry*, vol. 42, No. 3, pp. 446-457.
Wawzonek, Stanley, "Novel Formation of 11-Ketoindeno[1,2-c]Isocoumarin," 1968, The Journal of Organic Chemistry, vol. 33, No. 2, pp: 896-897.
Wawzonek, Stanley, "Synthesis of 6-Substituted-6H-Indeno[1,2-c] Isoquinoline-5,11-diones," 1982, Database CA, Chemical Abstracts Service, Database Accession No. 1982:199485.
Cushman, Mark, and Prem Mohan. "Synthesis and antitumor activity of structural analogs of the anticancer benzophenanthridine alkaloid fagaronine chloride." *Journal of medicinal chemistry* 28.8 (1985): 1031-1036.
Wawzonek, S., J. K. Stowell, and R. E. Karll. "The Synthesis and Reactions of 1-Carbamyl-11-ketoindeno [1, 2-c] isoquinoline1." *The Journal of Organic Chemistry* 31.4 (1966): 1004-1006.
Cushman, Mark, Prem Mohan, and Edward CR Smith. "Synthesis and biological activity of structural analogs of the anticancer benzophenanthridine alkaloid nitidine chloride." *Journal of medicinal chemistry* 27.4 (1984): 544-547.
PCT Search Report and Written Opinion Prepared for PCT/US2011/022732, mailed Mar. 28, 2011.
Song, Yunlong, and Mark Cushman. "The Binding Orientation of a Norindenoisoquinoline in the Topoisomerase I—DNA Cleavage Complex Is Primarily Governed by π-π Stacking Interactions." *The Journal of Physical Chemistry B* 112.31 (2008): 9484-9489.
Ioanoviciu, Alexandra, et al. "Synthesis and mechanism of action studies of a series of norindenoisoquinoline topoisomerase I poisons reveal an inhibitor with a flipped orientation in the ternary DNA-enzyme-inhibitor complex as determined by X-ray crystallographic analysis." *Journal of medicinal chemistry* 48.15 (2005): 4803-4814.
Song, Yunlong, et al. "Structure-based design, synthesis, and biological studies of new anticancer norindenoisoquinoline topoisomerase I inhibitors." *Journal of medicinal chemistry* 53.5 (2010): 1979-1989.
Gensler, Walter J., Kolla T. Shamasundar, and Stephen Marburg. "Synthesis of 11H-indeno [1, 2-c] isoquinoline compounds related to chelerythrine." *The Journal of Organic Chemistry* 33.7 (1968): 2861-2868.
Jagtap, Prakash G., et al. "Facile and Convenient Syntheses of 6, 11-Dihydro-5 H-indeno [1, 2-c] isoquinolin-5-ones and 6, 11-Dihydro-5 H-indolo [3, 2-c] isoquinolin-5-one." *Organic letters* 7.9 (2005): 1753-1756.
Birch et al., "A New Modification of the Pomeranz-Fritsch Isoquinoline Synthesis", J. Chem. Soc., Perkin Trans. 1, 1974, pp. 2185-2190.
Pathak et al., "Enzymatic protecting group techniques in organic synthesis", Stereosel. Biocatal., 2000, pp. 775-797.
Gensler, "The synthesis of isoquinolones by the pomeranz-fritsch reaction", Org. React. 1951, 6, pp. 191-206.
Comins et al., "Ortho Metalation Directed by alpha-amino alkoxides", J. Org. Chem., 1984, 49, 1078-1083.
Boyd et al., "Some practical considerations and applications of the national cancer institute in vitro anticancer drug discovery screen", Drug Development Res., 1995, 34, pp. 91-109.
Shoemaker, "The NCI60 human tumour cell line anticancer drug screen", Nat. Rev. Cancer 2006, 6, 813-823.
Dexheimer et al., "DNA cleavage assay for the identification of topoisomerase I inhibitors", Nat. Protocol. 2008, 3, 1736-1750.
Balogh et al., "Comparative evaluation of in Silico pKa prediction tools on the gold standard dataset", QSAR Comb. Sci. 2009, 28, 1148-1155.
Akine et al. "Helical metallohost-guest complexes via site-selective transmetalation of homotrinuclear complexes", J. Am. Chem., Soc., 2006, 128, 15765-15774.
Barb et al. "Uridine-based inhibitors as new leads for antibiotics targeting Escherichia coli LpxC", Biochemistry, 2009, 48, 3068-3077.
Chung et al. "Impact of linker strain and flexibility in the design of a fragment-based inhibitor", Nature Chemical Biology, 2009, 5(6), 407-413.
Minutolo et al. "Salicylaldoxime moiety as a phenolic "A-ring" substitute in estrogen receptor ligands", J. Med. Chem., 2001, 44, 4288-4291.

* cited by examiner

SUBSTITUTED NORINDENOISOQUINOLINES, SYNTHESES THEREOF, AND METHODS OF USE

CROSS-REFERENCE TO RELATED APPLICATIONS

This application is a national stage entry under 35 USC §371(b) of International Application No. PCT/US2011/022732, filed Jan. 27, 2011, which claims priority under 35 U.S.C §119(e) to U.S. Provisional Application Ser. No. 61/298,789, filed on Jan. 27, 2010, the disclosures of which are incorporated by reference in their entirety.

GOVERNMENT RIGHTS

This invention was made with government support under Grant No. U01-CA89566 awarded by National Institutes of Health. The government has certain rights in the invention.

TECHNICAL FIELD

The invention described herein pertains to substituted norindenoisoquinoline compounds, and pharmaceutical compositions and formulations comprising the norindenoisoquinoline compounds. The invention described herein also pertains to methods for using the compounds described herein for the treatment and/or prevention of topoisomerase mediated diseases, such as cancer.

BACKGROUND AND SUMMARY OF THE INVENTION

DNA topoisomerase I (Top1) is believed to be an important target for the design of novel antitumor drugs. It is a ubiquitous and essential nuclear enzyme for DNA replication and transcription. As a class, the Top1 inhibitors in the camptothecin (1) family (CPTs) have been reported to suffer from poor water-solubility, high toxicity, and metabolic instability. Subsequent efforts to improve the limitations of 1 have lead to topotecan (2) and irinotecan (3).

However, is believed herein that additional improvements in this class of molecules is needed. For example, this family made be limited by the E-ring of the CPTs, which contains an α-hydroxylactone that opens to a hydroxycarboxylate that binds tightly to serum albumin; and the drug-target interaction, which is reversible and has to be maintained long enough to convert Top1 cleavage complexes into DNA damage. In addition, it has been reported that several Top1 resistance mutations such as Asn722Ser and Arg364His occur; tumor cells that over-express drug efflux pumps are becoming resistant to CPTs; and the occurrence of side effects caused by CPTs, which may limit the doses that can be safely administered and, therefore, antitumor efficacy.

It has been discovered that the norindenoisoquinolines described herein are potent cytotoxic agents, and modulators of topoisomerase I.

In one illustrative embodiment of the invention, compounds of the following formula are described herein

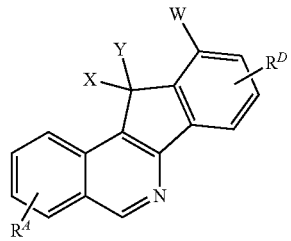

and pharmaceutically acceptable salts thereof, wherein $R^A$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ includes at least two adjacent substituents that are taken together with the attached carbons to form an optionally substituted heterocycle;

$R^D$ represents three substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ includes at least two adjacent substituents that are taken together with the attached carbons to form an optionally substituted heterocycle;

X and Y are each independently selected from the group consisting of hydrogen, and hydroxy, amino, hydroxylamino, and hydrazino, and derivatives thereof, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, or alkylidenyl, each of which is optionally substituted; and W is a hydrophilic group.

In another illustrative embodiment, compounds of the following formula are described herein

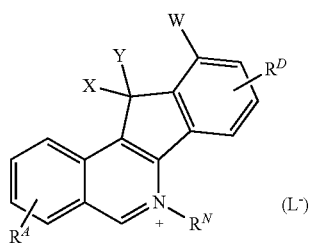

and pharmaceutically acceptable salts thereof, wherein $R^A$, $R^D$, W, X, and Y are as defined in the various embodiments described herein; and $R^N$ is hydrogen, or hydroxy, amino, or thio, or a derivative thereof, or acyl, sulfoxyl, sulfonyl, phosphinyl, or phosphonyl, or $CO_2H$, $SO_2H$, $SO_3H$, $PO_2H$, or $PO_3H$, or a derivative thereof, or alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted; and (L⁻) is a pharmaceutically acceptable anion.

Without being bound by theory, it is believed herein that the compounds described herein may be highly efficacious because of the increased water solubility provided by the group W.

It has also been discovered that the norindenoisoquinolines described herein may have different Top1 cleavage patterns than other compounds, such as the CPTs and indenoisoquinolines that have been reported. Without being bound by theory, it is believed herein that this difference may indicate that different cancer cell genes could be targeted more selectively with norindenoisoquinolines.

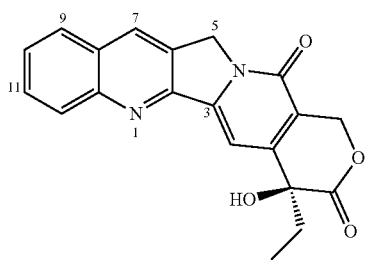

Figure 1:
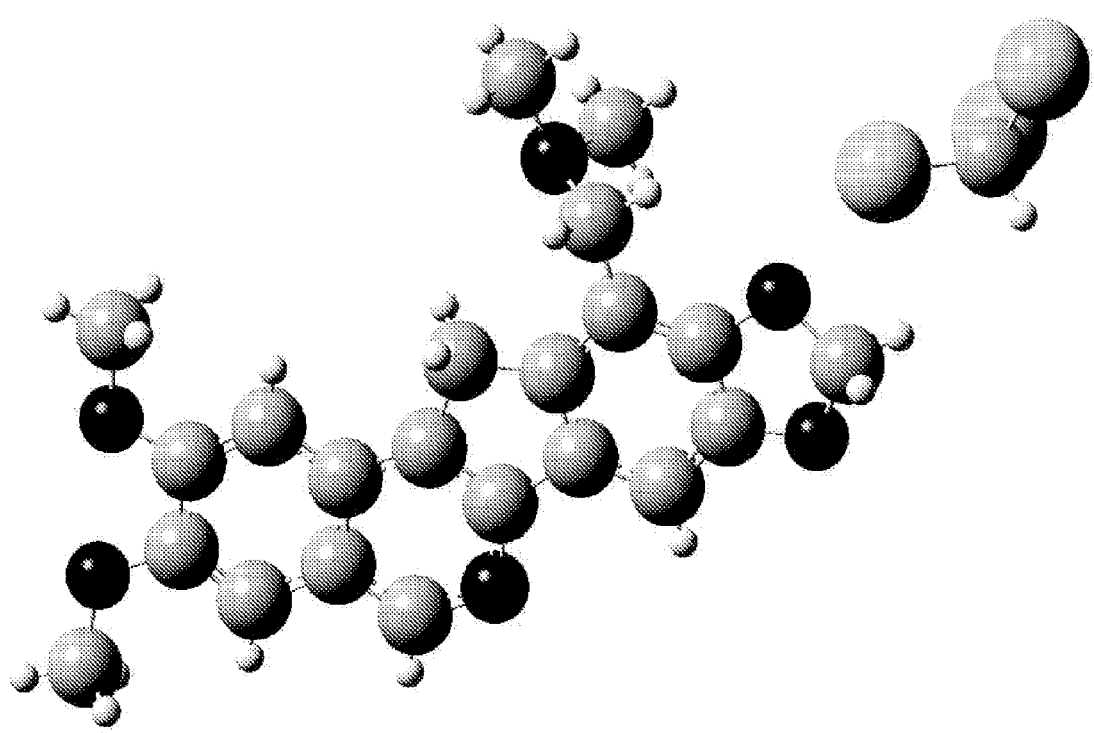
FIG. 1. Crystal structure of norindenoisoquinoline 14a (the neighboring solvent molecule is chloroform).

(lane 4) MJ-III-65 (Birch et al., R., New Modification of the Pomeranz-Fritsch Isoquinoline Synthesis. J. Chem. Soc., Perkin Trans. 1 1974, 2185-2190), 1 μM;

MJ-III-65

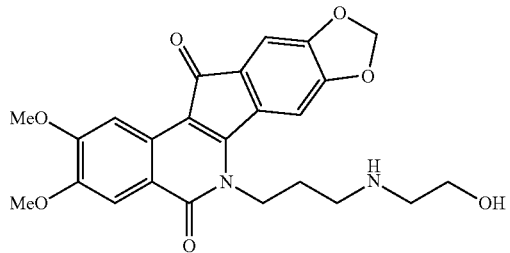

(lanes 5-36) comparison compound 5

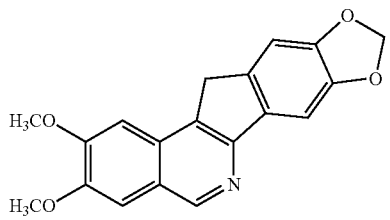

(Ioanoviciu et al., Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex as Determined by X-ray Crystallographic Analysis. J. Med. Chem. 2005, 48, 4803-4814), comparison compound 15, and compounds 14a-f, Top 1+indicated compound at 0.1, 1, 10, and 100 μM, respectively. The numbers on the right and arrows indicate cleavage site positions. A 117-bp DNA substrate was used in this assay; however, the cleavage sites are numbered to be consistent with the 161-bp DNA substrate traditionally used in this assay in order to facilitate comparison.

DETAILED DESCRIPTION

It has been discovered herein that substituted norindenoisoquinoline compounds and pharmaceutical compositions and formulations comprising these compounds are useful in the treatment and/or prevention of cancer. In one aspect, the substituted norindenoisoquinolines include substitution on the 10-position.

In one embodiment, described herein is a compound of the formula

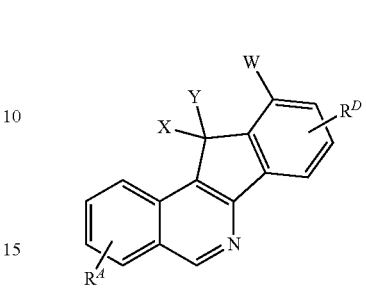

or a pharmaceutically acceptable salt thereof, wherein
$R^A$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ includes at least two adjacent substituents that are taken together with the attached carbons to form an optionally substituted heterocycle;
$R^D$ represents three substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ includes at least two adjacent substituents that are taken together with the attached carbons to form an optionally substituted heterocycle;
X and Y are each independently selected from the group consisting of hydrogen, and hydroxy, amino, hydroxylamino, and hydrazino, and derivatives thereof, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, and alkylidenyl, each of which is optionally substituted; and W is a hydrophilic group.

In another embodiment, described herein is a compound of the formula

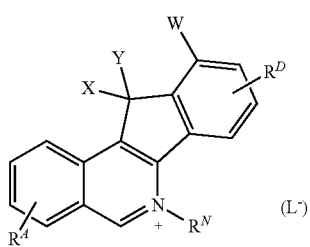

or a pharmaceutically acceptable salt thereof, wherein $R^A$, $R^D$, W, X, Y are as defined above;

$R^N$ is hydrogen, or hydroxy, amino, or thio, or a derivative thereof, or acyl, sulfoxyl, sulfonyl, phosphinyl, or phosphonyl, or $CO_2H$, $SO_2H$, $SO_3H$, $PO_2H$, or $PO_3H$, or a derivative thereof, or alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted; and ($L^-$) is a pharmaceutically acceptable anion.

In another embodiment, compounds are described wherein $R^N$ as recited in each of the other embodiments described herein is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, and optionally substituted acyl;

In another embodiment, described herein is a compound as recited in each of the other embodiments described herein wherein $R^N$ is $(CH_2)_n$—$Z^a$, where n is an integer from 1-6, and $Z^a$ is selected from halo, hydroxy, alkoxy, cycloalkoxy, haloalkoxy, halocycloalkoxy, optionally substituted aryloxy, optionally substituted heteroaryloxy, acyloxy, amino, alkyl and dialkylamino, trialkylammonium, hydroxyalkylamino, hydroxyalkylaminoalkylamino, acylamino, hydroxylamino, alkoxylamino, acyloxylamino, cycloalkyl, heteroaryl, halocycloalkyl, alkenyl, alkynyl, acyl, cyano, nitro, azido, thio, alkylsulfonyl, carboxylic acid and derivatives thereof, sulfonic acid and derivatives thereof, and phosphonic acid and derivatives thereof.

In another embodiment, described herein is a compound as recited in each of the other embodiments described herein wherein $Z^a$ is dialkylamino, including dimethylamino, azido, poly(hydroxyalkyl)amino, hydroxyalkylaminoalkylamino, polyhydroxyalkylaminoalkylamino, hydroxyalkyl(alkylamino), or heteroaryl, where each alkyl is independently selected.

In another embodiment, described herein is a compound as recited in each of the other embodiments described herein wherein $Z^a$ is a radical selected from the group of formulae consisting of

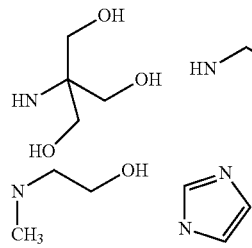

each of which may be optionally substituted.

In another embodiment, described herein is a compound as recited in each of the other embodiments described herein wherein m is 2, 3, or 4.

In another embodiment, described herein is a compound as recited in each of the other embodiments described herein wherein $R^N$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, or hydroxyalkyl(alkylamino), or a combinations thereof.

In another embodiment, described herein is a compound as recited in each of the other embodiments described herein wherein $R^N$ is hydrogen.

In another embodiment, described herein is a compound as recited in each of the other embodiments described herein wherein $R^N$ is substituted $C_1$-$C_4$ alkyl.

In another embodiment, described herein is a compound as recited in each of the other embodiments described herein wherein $R^N$ is substituted $C_3$ alkyl.

In another embodiment, described herein is a compound of the formula

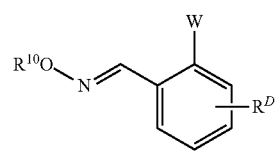

or a salt thereof, wherein $R^D$ represents three substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ includes at least two adjacent substituents that are taken together with the attached carbons to form an optionally substituted heterocycle;

W is a hydrogen; or a hydrophilic group, or a synthetic precursor thereof, such as a prodrug group or protecting group; and $R^{10}$ is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted.

In another embodiment of the foregoing embodiment, W is a hydrophilic group, or a synthetic precursor thereof, such as a prodrug group or protecting group. In another embodiment of the foregoing embodiment, W is a hydrophilic group.

In another embodiment, described herein is a process for preparing a compound of the formulae

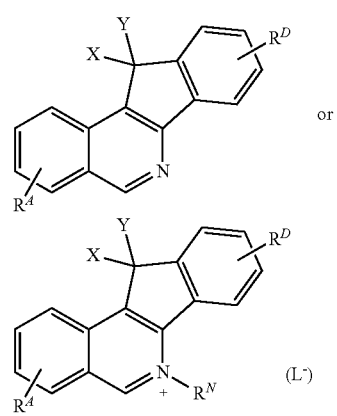

or a pharmaceutically acceptable salt thereof, wherein $R^A$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ includes at least two adjacent substituents that are taken together with the attached carbons to form an optionally substituted heterocycle;

$R^D$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ includes at least two adjacent substituents that are taken together with the attached carbons to form an optionally substituted heterocycle;

X and Y are each independently selected from the group consisting of hydrogen, and hydroxy, amino, hydroxylamino, and hydrazino, and derivatives thereof, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, or alkylidenyl, each of which is optionally substituted;

$R^N$ is hydrogen, or hydroxy, amino, or thio, or a derivative thereof, or acyl, sulfoxyl, sulfonyl, phosphinyl, or phosphonyl, or $CO_2H$, $SO_2H$, $SO_3H$, $PO_2H$, or $PO_3H$, or a derivative thereof, or alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted; and (L$^-$) is a pharmaceutically acceptable anion.

the process comprising the step of treating a compound of formula

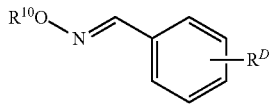

with a compound of formula

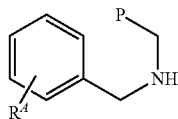

and an acid; wherein $R^{10}$ is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted; and P is an aldehyde or protected aldehyde, such as an acetal.

In another embodiment of the process, one of $R^D$ is W; where W is a hydrogen; or a hydrophilic group, or a synthetic precursor thereof, such as a prodrug group or protecting group, at C-10. In another embodiment of the process, one of $R^D$ is W; where W is a hydrophilic group, or a synthetic precursor thereof, such as a prodrug group or protecting group, at C-10. In another embodiment of the process, one of $R^D$ is W; where W is a hydrophilic group at C-10.

In another embodiment, described herein is the compound as recited in each of the other embodiments described herein wherein W is a radical of the formula $(CH_2)_m$—Z, where m is an integer from 0 to about 6; and Z is hydroxy, amino, nitro, or alkyl, alkenyl, cycloalkyl, carbaryl, or carbarylalkyl, each of which is substituted with hydroxy, amino, or nitro, or a combination thereof, or heteroalkyl, cycloheteroalkyl, heteroaryl, or heteroarylalkyl, each of which is optionally substituted.

In another embodiment, described herein is a compound as recited in each of the other embodiments described herein wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted.

In another embodiment, described herein is a compound as recited in each of the other embodiments described herein wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted; providing that $(CH_2)_m$—Z is not methyl.

In another embodiment, described herein is a compound as recited in each of the other embodiments described herein wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted; providing that $(CH_2)_m$—Z is not methyl or ethyl.

In another embodiment, described herein is a compound as recited in each of the other embodiments described herein wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted; providing that $(CH_2)_m$—Z is not unsubstituted alkyl.

In another embodiment, described herein is the compound as recited in each of the other embodiments described herein wherein Z is hydroxy, amino, nitro, or alkyl, alkenyl, heteroalkyl, cycloalkyl, cycloheteroalkyl, aryl, or arylalkyl, each of which is substituted; where said substituents include hydroxy, amino, or nitro, or a combination thereof.

In another embodiment, described herein is the compound as recited in each of the other embodiments described herein wherein Z is hydroxy, amino, nitro, or alkyl, alkenyl, cycloalkyl, carbaryl, or carbarylalkyl, each of which is substituted with hydroxy, amino, or nitro, or a combination thereof.

In another embodiment, described herein is a compound as recited in each of the other embodiments described herein wherein Z is a nitrogen substituted alkyl, alkenyl, cycloalkyl, aryl, or arylalkyl; or a nitrogen containing heteroalkyl, cycloheteroalkyl, aryl, or arylalkyl, each of which is optionally substituted.

In another embodiment, described herein is a compound as recited in each of the other embodiments described herein wherein Z is hydroxy, amino, or aminoalkylamino, hydroxyalkylamino, aminoalkylaminoalkylamino, or hydroxyalkylaminoalkylamino, each of which is optionally substituted.

In another embodiment, described herein is a compound as recited in each of the other embodiments described herein wherein Z is heterocyclyl, heterocyclylalkylamino, or heterocyclylalkylaminoalkylamino, each of which is optionally substituted.

In another embodiment, described herein is a compound as recited in each of the other embodiments described herein wherein Z is heteroaryl, heteroarylalkylamino, or heteroarylalkylaminoalkylamino, each of which is optionally substituted.

In another embodiment, described herein is a compound as recited in each of the other embodiments described herein wherein Z is dialkylamino, dialkylaminoalkylamino, or dialkylaminoalkyl(alkylamino), where each alkyl is independently selected.

In another embodiment, described herein is a compound as recited in each of the other embodiments described herein wherein Z is optionally substituted heterocyclyl, where the heterocyclyl is pyrrolidinyl, piperidinyl, piperazinyl, homopiperazinyl, or morpholinyl.

In another embodiment, described herein is a compound as recited in each of the other embodiments described herein wherein Z is optionally substituted imidazole.

In another embodiment, described herein is a compound as recited in each of the other embodiments described herein wherein Z is alkyl substituted with a sulfonyl, sulfinyl, phosphoryl, phosphonyl, or phosphinyl group.

In another embodiment, described herein is a compound as recited in each of the other embodiments described herein wherein m is 1, 2, or 3. In another embodiment, described herein is a compound of the formulae above wherein m is 1.

In another embodiment, described herein is a compound as recited in each of the other embodiments described herein wherein X and Y are both hydrogen.

In another embodiment, described herein is a compound as recited in each of the other embodiments described herein wherein X is hydrogen, optionally substituted alkyl, optionally substituted alkenyl, optionally substituted alkynyl, optionally substituted arylalkyl, optionally substituted heteroarylalkyl, OR, NROR, and NRNRR, where R is in each instance independently selected from hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl; and Y is hydrogen or alkyl.

In another embodiment, described herein is a compound as recited in each of the other embodiments described herein wherein X and Y are taken together to form a double-bonded substituent selected from oxygen, optionally substituted alken-1-yl, NOR, and NNRR, where R is in each instance independently selected from hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl.

In another embodiment, described herein is a compound as recited in each of the other embodiments described herein wherein X and Y are taken together to form a double-bonded oxygen.

In another embodiment, described herein is a compound as recited in each of the other embodiments described herein wherein $R^A$ represents four substituents each independently selected from the group consisting of hydrogen, and a radical $(CH_2)_mZ$, where m is an integer from 0-6 and Z is selected from the group consisting of halo, OH, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^5R^6$, $P(O)(OR^4)_2$, $P(O)(NR^4R^5)_2$, and $P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is a compound as recited in each of the other embodiments described herein wherein $R^A$ represents four substituents each independently selected from consisting of hydrogen and a radical $(CH_2)_mZ$, where m is an integer from 0-6 and Z is selected from the group consisting of halo, OH, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^5R^6$, $P(O)(OR^4)_2$, $P(O)(NR^4R^5)_2$, and $P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is a compound as recited in each of the other embodiments described herein wherein $R^A$ represents four substituents where two of said substituents are adjacent substituents and are taken together with the attached carbons to form an optionally substituted heterocycle, and the remaining two substituents are each independently selected from the group consisting of hydrogen and a radical $(CH_2)_mZ$, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^5R^6$, $P(O)(OR^4)_2$, $P(O)(NR^4R^5)_2$, and $P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is a compound as recited in each of the other embodiments described herein wherein $R^A$ represents four substituents each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof.

In another embodiment, described herein is a compound as recited in each of the other embodiments described herein wherein $R^A$ represents four substituents where two of said substituents are adjacent substituents and are taken together with the attached carbons to form an optionally substituted heterocycle, and where the two remaining substituents are each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof.

In another embodiment, described herein is a compound as recited in each of the other embodiments described herein wherein $R^A$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, bis(hydroxyalkyl)amino, hydroxyalkylaminoalkylamino, heteroarylalkylaminoalkylamino, acylamino, hydroxylamino, alkoxylamino, acyloxyamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof.

In another embodiment, described herein is a compound as recited in each of the other embodiments described herein wherein $R^A$ includes two substituents selected from the group consisting of halo, hydroxy, nitro, and optionally substituted alkoxy.

In another embodiment, described herein is a compound as recited in each of the other embodiments described herein wherein $R^A$ includes two substituents taken together with the attached carbons that form an optionally substituted heterocycle. In another embodiment, described herein is a compound of the formulae above wherein the heterocycle is a 1,3-dioxolane or a 1,4-dioxane.

In another embodiment, described herein is a compound as recited in each of the other embodiments described herein wherein $R^A$ is bismethoxy or methylenedioxy.

In another embodiment, described herein is a compound as recited in each of the other embodiments described herein wherein $R^A$ represents four substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^A$ includes at least two adjacent substituents that are taken together with the attached carbons to form an optionally substituted heterocycle.

In another embodiment, described herein is a compound as recited in each of the other embodiments described herein wherein $R^D$ represents three substituents each independently selected from the group consisting of hydrogen, and a radical $(CH_2)_mZ$, where m is an integer from 0-6 and Z is selected from the group consisting of halo, OH, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^5R^6$, $P(O)(OR^4)_2$, $P(O)(NR^4R^5)_2$, and $P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is a compound as recited in each of the other embodiments described herein wherein $R^D$ represents three substituents each independently selected from consisting of hydrogen and a radical $(CH_2)_mZ$, where m is an integer from 0-6 and Z is selected from the group consisting of halo, OH, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, $NH_2$, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^5R^6$, $P(O)(OR^4)_2$, $P(O)(NR^4R^5)_2$, and $P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is a compound as recited in each of the other embodiments described herein wherein $R^D$ represents three substituents where two of said substituents are adjacent substituents and are taken together with the attached carbons to form an optionally substituted heterocycle, and the remaining two substituents are each independently selected from the group consisting of hydrogen and a radical $(CH_2)_mZ$, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $N_3$, $CO_2R^4$, $CONR^5R^6$, $P(O)(OR^4)_2$, $P(O)(NR^4R^5)_2$, and $P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

In another embodiment, described herein is a compound as recited in each of the other embodiments described herein wherein $R^D$ represents three substituents each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof.

In another embodiment, described herein is a compound as recited in each of the other embodiments described herein wherein $R^D$ represents three substituents where two of said substituents are adjacent substituents and are taken together with the attached carbons to form an optionally substituted heterocycle, and where the two remaining substituents are each independently selected from the group consisting of hydrogen, halo, OH, optionally substituted alkyl, optionally substituted alkoxy, cyano, nitro, optionally substituted alkylthio, optionally substituted alkylsulfonyl, $CO_2H$ and derivatives thereof, and $SO_3H$ and derivatives thereof.

In another embodiment, described herein is a compound as recited in each of the other embodiments described herein wherein $R^D$ includes two substituents selected from the group consisting of halo, hydroxy, nitro, and optionally substituted alkoxy.

In another embodiment, described herein is a compound as recited in each of the other embodiments described herein wherein $R^D$ includes two substituents taken together with the attached carbons that form an optionally substituted heterocycle.

In another embodiment, described herein is a compound as recited in each of the other embodiments described herein wherein the heterocycle is a 1,3-dioxolane or a 1,4-dioxane.

In another embodiment, described herein is a compound as recited in each of the other embodiments described herein wherein $R^D$ is bismethoxy or methylenedioxy.

In another embodiment, described herein is a compound as recited in each of the other embodiments described herein wherein $R^D$ represents three substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^D$ includes at least two adjacent substituents that are taken together with the attached carbons to form an optionally substituted heterocycle.

In another embodiment, described herein is a compound as recited in each of the other embodiments described herein wherein $R^A$ or $R^D$, or both $R^A$ and $R^D$ includes hydroxy or a derivative thereof selected from the group consisting of OH, alkoxy, alkylsulfoxy, arylsulfoxy, and arylalkylsulfoxy.

In another embodiment, described herein is a compound as recited in each of the other embodiments described herein wherein $R^A$ or $R^D$, or both $R^A$ and $R^D$ includes amino or a derivative thereof selected from the group consisting of $NH_2$, alkylamino, dialkylamino, acylamino, and sulfonylamino, where alkyl is independently selected in each instance.

In another embodiment, described herein is a compound as recited in each of the other embodiments described herein wherein $R^A$ or $R^D$, or both $R^A$ and $R^D$ includes thio or a derivative thereof selected from the group consisting of SH, and alkylthio.

In another embodiment, described herein is a compound as recited in each of the other embodiments described herein wherein $R^A$ or $R^D$, or both $R^A$ and $R^D$ includes sulfonyl selected from the group consisting of alkylsulfonyl, arylsulfonyl, and arylalkylsulfonyl.

In another embodiment, described herein is a compound as recited in each of the other embodiments described herein wherein $R^A$ or $R^D$, or both $R^A$ and $R^D$ includes phosphonyl selected from the group consisting of alkylphosphonyl, arylphosphonyl, and arylalkylphosphonyl.

In another embodiment, described herein is a compound as recited in each of the other embodiments described herein wherein $R^A$ or $R^D$, or both $R^A$ and $R^D$ includes $CO_2H$ or a derivative thereof selected from the group consisting of CN, $CO_2M$, where M is a pharmaceutically acceptable cation, an ester, and an amide.

In another embodiment, described herein is a compound as recited in each of the other embodiments described herein wherein $R^A$ is 2,3-bismethoxy; and $R^D$ is 8,9-methylenedioxy.

In another embodiment, described herein is a composition comprising one or more compounds as recited in each of the other embodiments described herein, and optionally one or more carriers, diluents, or excipients, or a combination thereof. In one aspect, the one or more compounds are present in a therapeutically effective amount for treating a disease responsive to inhibition of topoisomerase 1. In another aspect, the disease is a cancer.

In another embodiment, described herein is a method for treating a patient having a disease responsive to inhibition of topoisomerase 1, the method comprising the step of administering a therapeutically effective amount of one or more compounds as recited in each of the other embodiments described herein or compositions comprising one or more compounds as recited in each of the other embodiments described herein to the patient. In another embodiment of this method, the disease is a cancer.

In another embodiment, compounds are described wherein $R^A$ as recited in each of the other embodiments described herein represents four substituents each independently selected from the group consisting of hydrogen, halo, hydroxy, amino, nitro, and alkyl, heteroalkyl, cycloalkyl, cycloheteroalkyl, aryl, arylalkyl, and alkoxy, each of which is optionally substituted, providing that when $R^A$ includes two adjacent substituents that are not hydrogen, said substituents are optionally taken together with the attached carbons to form an optionally substituted heterocycle;

$R^D$ as recited in each of the other embodiments described herein represents three substituents each independently selected from the group consisting of hydrogen, halo, hydroxy, amino, nitro, and alkyl, heteroalkyl, cycloalkyl, cycloheteroalkyl, aryl, arylalkyl, and alkoxy, each of which is optionally substituted, providing that when $R^A$ includes two adjacent substituents that are not hydrogen, said substituents are optionally taken together with the attached carbons to form an optionally substituted heterocycle;

X and Y as recited in each of the other embodiments described herein are both hydrogen; and W as recited in each of the other embodiments described herein is a hydrophilic group.

In another embodiment, described herein is a compound as recited in each of the other embodiments described herein, wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted.

In another embodiment, described herein is a compound as recited in each of the other embodiments described herein, wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted; providing that $(CH_2)_m$—Z is not methyl.

In another embodiment, described herein is a compound as recited in each of the other embodiments described herein, wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted; providing that $(CH_2)_m$—Z is not methyl or ethyl.

In another embodiment, described herein is a compound as recited in each of the other embodiments described herein, wherein W is a radical of the formula $(CH_2)_m$—Z, where m is an integer from 0 to about 6; and Z is hydroxy, amino, nitro, or alkyl, alkenyl, heteroalkyl, cycloalkyl, cycloheteroalkyl, aryl, or arylalkyl, each of which is optionally substituted; providing that $(CH_2)_m$—Z is not unsubstituted alkyl.

In another embodiment, described herein is a compound as recited in each of the other embodiments described herein, wherein Z is a nitrogen substituted alkyl, alkenyl, cycloalkyl, aryl, or arylalkyl; or a nitrogen containing heteroalkyl, cycloheteroalkyl, aryl, or arylalkyl, each of which is optionally substituted.

In another embodiment, described herein is a compound as recited in each of the other embodiments described herein, wherein Z is hydroxy, amino, or aminoalkylamino, hydroxyalkylamino, aminoalkylaminoalkylamino, or hydroxyalkylaminoalkylamino, each of which is optionally substituted.

In another embodiment, described herein is a compound as recited in each of the other embodiments described hereinabove, wherein Z is heterocyclyl, heterocyclylalkylamino, or heterocyclylalkylaminoalkylamino, each of which is optionally substituted.

In another embodiment, described herein is a compound as recited in each of the other embodiments described herein, wherein Z is heteroaryl, heteroarylalkylamino, or heteroarylalkylaminoalkylamino, each of which is optionally substituted.

In another embodiment, described herein is a compound as recited in each of the other embodiments described herein, wherein Z is dialkylamino, dialkylaminoalkylamino, or dialkylaminoalkyl(alkylamino), where each alkyl is independently selected.

In another embodiment, described herein is a compound as recited in each of the other embodiments described herein, wherein Z is optionally substituted heterocyclyl, where the heterocyclyl is pyrrolidinyl, piperidinyl, piperazinyl, homopiperazinyl, or morpholinyl.

In another embodiment, described herein is a compound as recited in each of the other embodiments described herein, wherein Z is optionally substituted imidazole.

In another embodiment, described herein is a compound as recited in each of the other embodiments described herein, wherein Z is alkyl substituted with a sulfonyl, sulfinyl, phosphoryl, phosphonyl, or phosphinyl group.

In another embodiment, described herein is a compound as recited in each of the other embodiments described herein, wherein m is 1, 2, or 3. In one aspect, m is 1.

In another embodiment, described herein is a compound as recited in each of the other embodiments described herein, wherein $R^A$ includes two substituents selected from the group consisting of halo, hydroxy, nitro, and optionally substituted alkoxy.

In another embodiment, described herein is a compound as recited in each of the other embodiments described herein, wherein $R^D$ includes two substituents selected from the group consisting of halo, hydroxy, nitro, and optionally substituted alkoxy.

In another embodiment, described herein is a compound as recited in each of the other embodiments described herein, wherein $R^A$ includes two substituents taken together with the attached carbons that form an optionally substituted heterocycle.

In another embodiment, described herein is a compound as recited in each of the other embodiments described herein, wherein $R^D$ includes two substituents taken together with the attached carbons that form an optionally substituted heterocycle. In one aspect, the heterocycle is a 1,3-dioxolane or a 1,4-dioxane.

In another embodiment, described herein is a compound as recited in each of the other embodiments described herein, wherein $R^A$ and $R^D$ are each independently selected from the group consisting of bismethoxy and methylenedioxy.

In another embodiment, described herein is the compound as recited in each of the other embodiments described herein for treating a disease responsive to inhibition of topoisomerase 1.

In another embodiment, described herein is a composition comprising one or more of the compounds as recited in each of the other embodiments described herein, and optionally one or more carriers, diluents, or excipients, or a combination thereof.

In another embodiment, described herein is a method for treating a disease responsive to inhibition of topoisomerase 1, the method comprising the step of administering one or more of the compounds or the compositions as recited in each of the other embodiments described herein to a patient having the disease. In one embodiment, the disease is a cancer.

In another embodiment, described herein is the use of the compound as recited in each of the other embodiments described herein in the manufacture of a medicament for treating a disease responsive to inhibition of topoisomerase 1. In one illustrative embodiment, the disease is a cancer.

In another embodiment, described herein are pharmaceutical compositions comprising one or more C-10 substituted norindenoisoquinolines described herein. The substituted norindenoisoquinoline and the pharmaceutical compositions comprising them are useful in the treatment of diseases such as cancer.

In another embodiment, described herein are methods of use of one or more C-10 substituted norindenoisoquinolines and/or pharmaceutical compositions comprising them for treating diseases responsive to topoisomerase I modulation, such as cancer. Illustratively, these methods include administering to a patient in need of relief from the disease a therapeutically effective amount of one or more of the substituted norindenoisoquinolines and/or pharmaceutical compositions comprising them. In one variation, the methods described herein include co-therapies with other therapeutic agents for treating the disease. Accordingly, the compounds, compositions, formulations and methods described herein may be combined with any one or more of the known compounds or agents. Such a co-therapy includes the co-administration of one or more of the compounds described herein and one or more of the known compounds or agents to a patient in need of relief.

In another embodiment, the substituted norindenoisoquinolines exhibit improved aqueous solubilities compared to other indenoisoquinolines and CPTs.

In another embodiment, substituted norindenoisoquinolines are described herein that exhibit nanomolar cytotoxicity against cancer cells. In another embodiment, substituted norindenoisoquinolines are described herein that exhibit cytotoxicity, such as nanomolar cytotoxicity, against one or more of human leukemia, ovarian, and/or breast cancer cells. In another embodiment, substituted norindenoisoquinolines are described herein that exhibit cytotoxicity, such as nanomolar cytotoxicity, against one or more of human colon and/or renal cancer cells. In another embodiment, substituted norindenoisoquinolines are described herein that act as Top1 poisons. In another embodiment, substituted norindenoisoquinolines are described herein that stabilize the Top1-DNA-inhibitor cleavage complex by inhibiting the religation reaction. Without being bound by theory, it is believed herein that the pattern of DNA cleavages observed with the compounds described herein may be different from known indenoisoquinolines and camptothecins, and be at least partially responsible the cytotoxicity profiles observed herein.

In another embodiment, processes are described for preparing the compounds described herein. Illustratively, the process includes a Pomeranz-Fritsch reaction (Gensler, The Synthesis of Isoquinolines by the Pomeranz-Fritsch Reaction. *Org. React.* 1951, 6, 191-206; the foregoing publication, and each additional publicated cited herein, is incorporated herein by reference) and/or an alternative version thereof, including the Bobbitt (Bobbitt et al., Synthesis of Isoquinolines. IV.[1] 4-Benzylisoquinolines. *J. Org. Chem.* 1965, 30, 2459-2460) and/or Jackson modification.

It is to be understood that, as used herein, the term "norindenoisoquinoline", as well as the various embodiments represented by the formulae described herein, generally refers to the parent compounds as well as pharmaceutically acceptable salts thereof, including acid and/or base addition salts. In addition, the term and representative formulae include hydrates and solvates thereof. In addition, the term and representative formulae include all morphological forms of the compound, including amorphous forms as well as any particular crystal morphology or mixture thereof. In addition, it is to be understood that various prodrugs of the compounds are described herein. For example, conventional prodrug groups may replace one or more heteroatom hydrogens, such as one present on an oxygen, nitrogen, sulfur, or phosphorus atom. Illustrative prodrug groups include, but are not limited to, those that may be present on one or more amino, hydroxyl, thio, and/or phosphate prodrugs.

It is to be understood that in each of the embodiments described herein, the physical state of the compounds may be amorphous, or in any of a variety of morphological forms. In addition, it is to be understood that the compounds described herein may each be included in the compositions and methods described herein as any number of a variety of pharmaceutical salt forms, or as a hydrate or other solvate.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including $C_1$-$C_{24}$, $C_1$-$C_{12}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain is cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, or arylalkyl, each of which is optionally substituted, it being understood herein that aryl includes carbaryl and heteroaryl.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^x$ is selected from $—CO_2R^4$ and $—CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$) alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein.

Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

It is understood herein that the dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

EXAMPLES

The following examples further illustrate specific embodiments of the invention; however, the following examples should not be interpreted in any way to limit the invention.

Process Examples

The syntheses of the compounds described herein, such as 14a-f and 15, are outlined in Schemes 1-3. It is to be understood that though the Schemes show particular compounds, such as particular values for substituents $R^A$, $R^D$, W, X, Y, $R^N$, and ($L^-$), the Schemes may be adapted for the preparation of other norindenoisoquinolines described herein by the appropriate selection of the corresponding starting materials.

Briefly, the synthesis is based on a Pomeranz-Fritsch reaction (Gensler, The Synthesis of Isoquinolines by the Pomeranz-Fritsch Reaction. *Org. React.* 1951, 6, 191-206) and its alternative versions including the Bobbitt and Jackson modifications. The required precursor 8 of the isoquinoline ring system was prepared as outlined in Scheme 1 (Ioanoviciu et al., Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex as Determined by X-ray Crystallographic Analysis. *J. Med. Chem.* 2005, 48, 4803-4814). Condensation of veratraldehyde (6) with aminoacetaldehyde dimethyl acetal resulted in formation of the Schiff base 7, which was reduced to the amine 8 with sodium borohydride in ethanol.

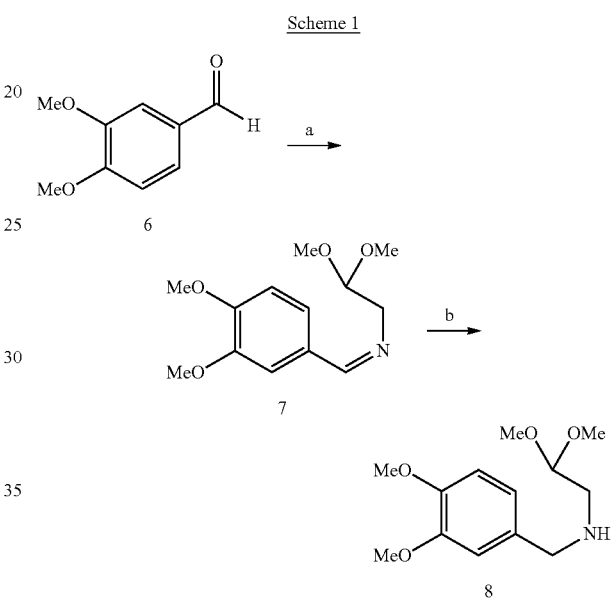

(a) $(MeO)_2CHCH_2NH_2$, PhH, 23° C. (4 h); (b) $NaBH_4$, EtOH, reflux (30 min).

As shown in Scheme 2, regioselective deprotonation of piperonal (9) with lithium N,N,N'-(trimethyl)ethylenediamine in THF resulted in a phenyllithium intermediate that was methylated to afford 2-methylpiperonal (10) (Comins & Brown, Ortho Metalation Directed by Alpha-Amino Alkoxides. *J. Org. Chem.* 1984, 49, 1078-1083). The aldehyde 10 was converted to its oxime ether 11, which was subjected to free radical bromination with NBS and AIBN in refluxing carbon tetrachloride to afford the benzyl bromide 12. Displacement of the bromide with various amines provided the penultimate intermediates 13a-f. Condensation of compounds 13a-f with intermediate 8 in concentrated hydrochloric acid at 100° C. yielded the final products 14a-f in low yields (3.1-7.8%).

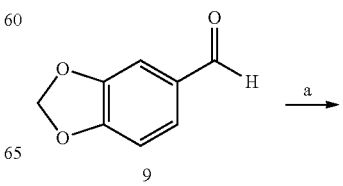

-continued

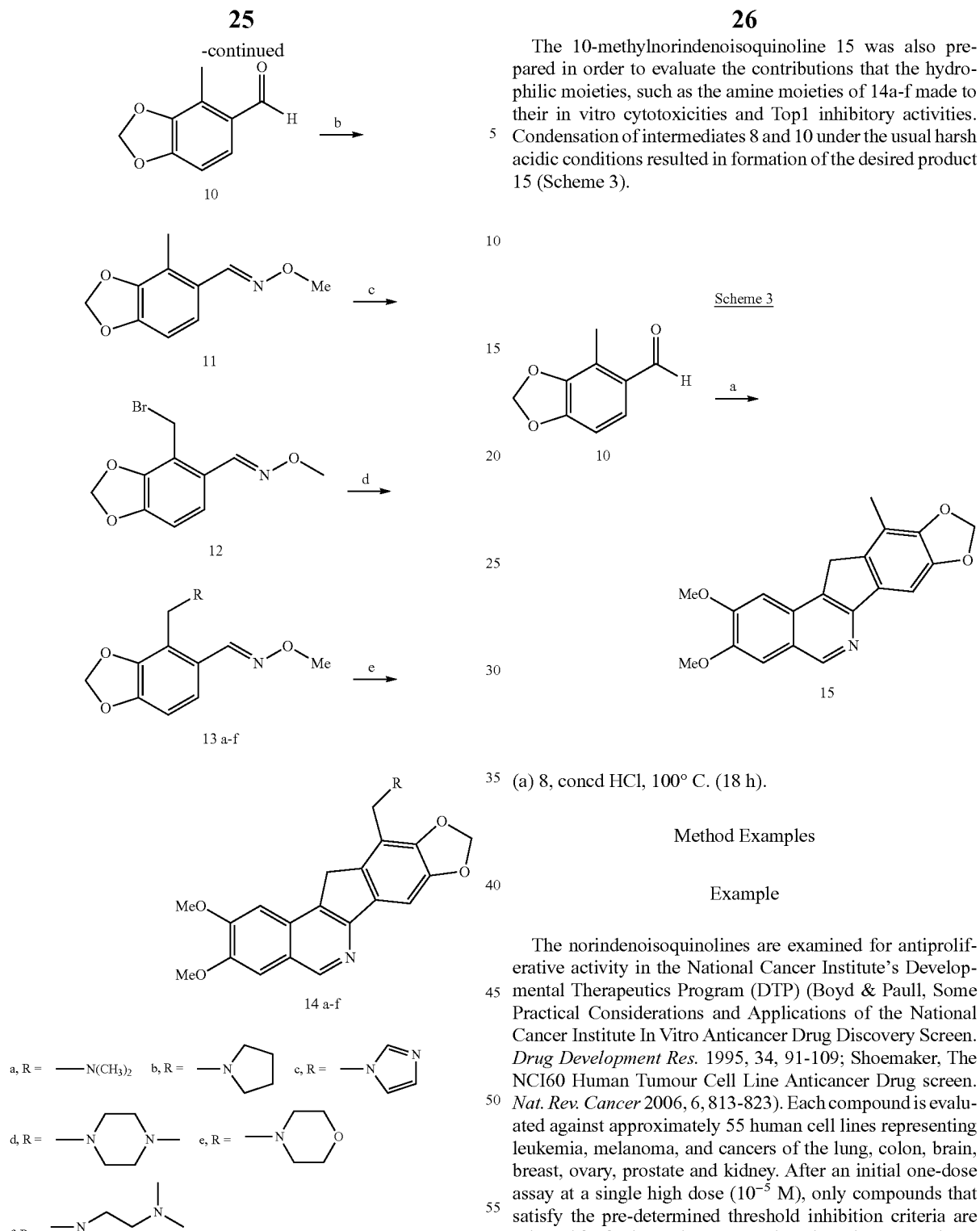

(a) (1) Me₂NCH₂CH₂NMeLi, THF, −78° C. (1 h), (2) MeI, −78° C. (2 h); (b) MeONH₃Cl⁻, NaOAc, MeOH, 23° C. (1 h); (c) NBS, AIBN, CCl₄, reflux (3 h); (d) amine, THF, 23° C.; (e) 8, concd HCl, 100° C.

It was observed that the reaction mixtures were complex and the yields were low due to both the formation of uncyclized 4-benzylisoquinolines and the subsequent purification methods.

The 10-methylnorindenoisoquinoline 15 was also prepared in order to evaluate the contributions that the hydrophilic moieties, such as the amine moieties of 14a-f made to their in vitro cytotoxicities and Top1 inhibitory activities. Condensation of intermediates 8 and 10 under the usual harsh acidic conditions resulted in formation of the desired product 15 (Scheme 3).

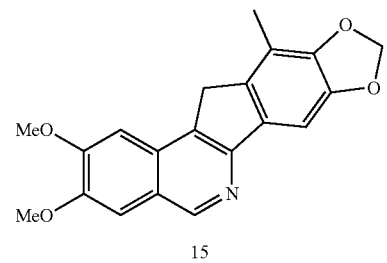

(a) 8, concd HCl, 100° C. (18 h).

Method Examples

Example

The norindenoisoquinolines are examined for antiproliferative activity in the National Cancer Institute's Developmental Therapeutics Program (DTP) (Boyd & Paull, Some Practical Considerations and Applications of the National Cancer Institute In Vitro Anticancer Drug Discovery Screen. *Drug Development Res.* 1995, 34, 91-109; Shoemaker, The NCI60 Human Tumour Cell Line Anticancer Drug screen. *Nat. Rev. Cancer* 2006, 6, 813-823). Each compound is evaluated against approximately 55 human cell lines representing leukemia, melanoma, and cancers of the lung, colon, brain, breast, ovary, prostate and kidney. After an initial one-dose assay at a single high dose ($10^{-5}$ M), only compounds that satisfy the pre-determined threshold inhibition criteria are selected for further 5-dose assay. The selected compounds are tested at five concentrations ranging from $10^{-8}$ M to $10^{-4}$ M. The $GI_{50}$ values from each subpanel are obtained with selected cell lines, and overall antiproliferative effects are quantified as a mean graph midpoint (MGM, Table 2). The MGM is a measure of the average $GI_{50}$ for all of the cell lines tested, in which $GI_{50}$ values below and above the test range ($10^{-8}$ M to $10^{-4}$ M) are taken as the minimum ($10^{-8}$ M) and maximum ($10^{-4}$ M) drug concentrations used in the assay. For comparison, the activity of camptothecin (1), is also listed in the table.

TABLE 2

Cytotoxicities and Topoisomerase I Inhibitory Activities of Norindenoisoquinolines

| compd | Cytotoxicity (GI$_{50}$ in μM)[a] | | | | | | | | | Top1 cleavage [c] |
|---|---|---|---|---|---|---|---|---|---|---|
| | Lung HOP-62 | Colon HCT-116 | CNS SF-539 | Melanoma UACC-62 | Ovarian OVCAR-3 | Renal SN12C | Prostate DU-145 | Breast MDA-MB-435 | MGM[b] | |
| CPT | 0.01 | 0.03 | 0.01 | 0.01 | 0.22 | 0.02 | 0.01 | 0.04 | 0.0405 | ++++ |
| 14a | 6.7 | 1.5 | 14 | 12 | 1.4 | 13 | 1.6 | 16 | 4.4 | +++ |
| 14b | 1.2 | 0.64 | 1.9 | 6.7 | 0.73 | 4.4 | 0.73 | 2.5 | 2.3 | +++ |
| 14c | 0.35 | 0.16 | 0.28 | 0.21 | 0.21 | 0.60 | 0.26 | NT[d] | 0.52 | +(+) |
| 14d[e] | | | | | | | | | | ++ |
| 14e | 2.1 | 1.4 | 1.8 | 100 | 1.7 | 2.3 | 1.9 | NT[d] | 2.4 | + |
| 14f | 1.5 | 1.9 | 11 | 0.73 | 7.4 | >100 | 3.4 | NT[d] | 6.3 | +(+) |
| 15 | 7.3 | 0.89 | 4.6 | 0.70 | 5.8 | >100 | >100 | >100 | 11.8 | ++ |

[a]The cytotoxicity of GI$_{50}$ values are the concentrations corresponding to 50% growth inhibition.
[b]Mean graph midpoint for growth inhibition of all human cancer cell lines successfully tested.
[c]The compounds were tested at concentrations ranging up to 10 uM. The activity of the compounds to produce Top1-mediated DNA cleavage was expressed semiquantitatively as follows: 0: no activity; +: weak activity; ++: similar activity as CPT; +++ and ++++: greater activity than CPT; ++++: similar activity as 1 uM CPT.
[d]NT = not tested.
[e]Not selected for further testing; refer to text for details.

It is observed that the compounds described herein show particularly potent activity on colon HCT-116 cancer cell and renal SN12C cancer cell cultures, compared to other norindenoisoquinolines. Without being bound by theory, it is believed herein that the inclusion of W at C-10 contributes to this improved activity.

Example

Norindenoisoquinoline 14c demonstrated nanomolar cytotoxicities against a series of human cancer cells, especially against leukemia, breast and ovarian cancer cells (Table 3). The GI$_{50}$ values of 14c against leukemia SR, CCRF-CEM, RPMI-8226 and MOLT-4 are 12 nM, 37 nM, 41 nM, 60 nM, respectively. It also displayed strong cytotoxicity against the human breast cancer cell MCF-7 with a GI$_{50}$ of 90 nM. This compound demonstrated a GI$_{50}$ of 121 nM against human ovarian cancer cell IGROVI.

Figure 2:
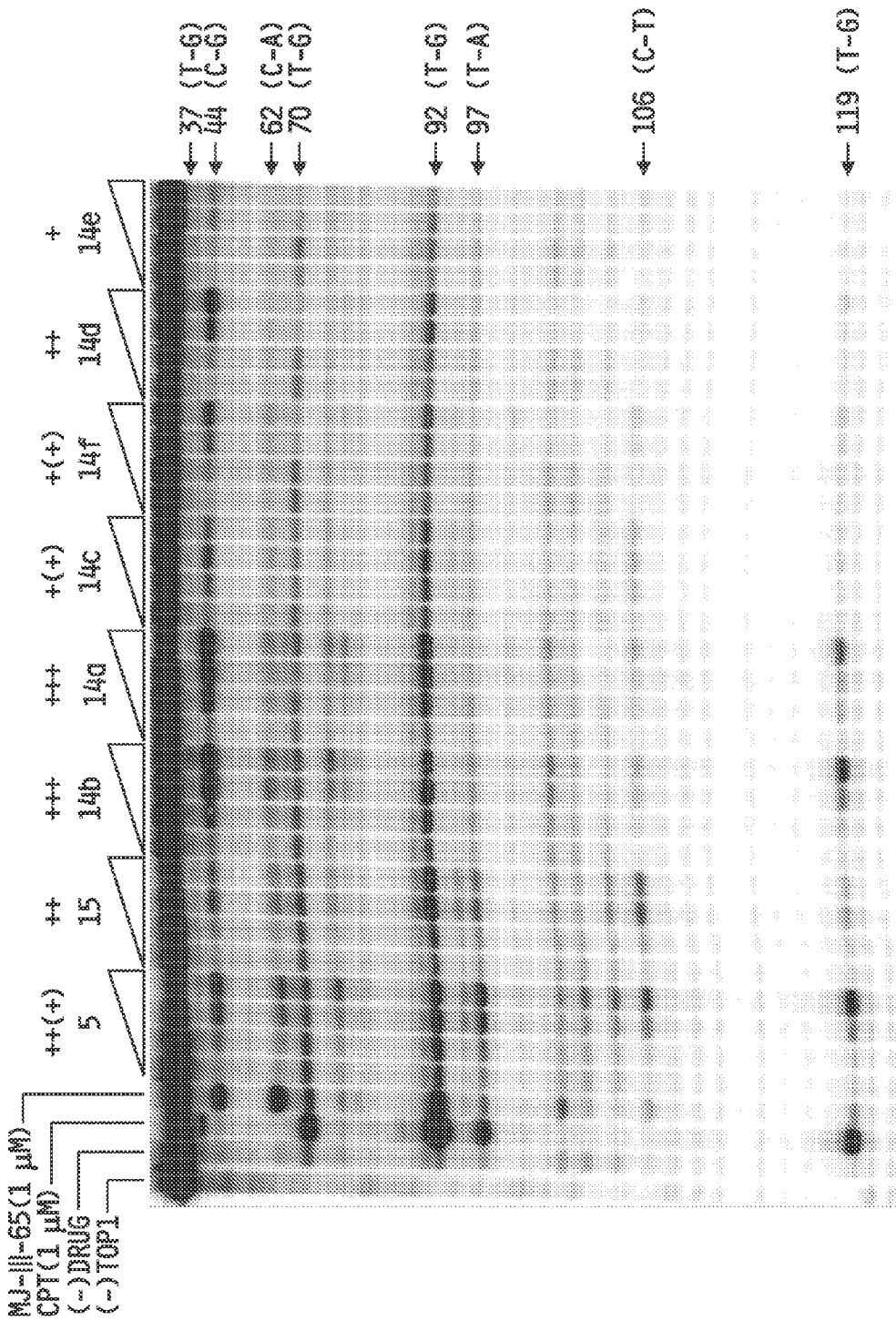
FIG. 2. Top1-mediated DNA cleavage induced by norindenoisoquinolines 14a-f: (lane 1) DNA alone; (lane 2) Top1 alone; (lane 3) camptothecin (1), 1 μM.

*Nat. Protocol.* 2008, 3, 1736-1750). The resulting gel electrophoresis DNA cleavage patterns are displayed in FIG. 2, along with comparison compounds.

It is observed that norindenoisoquinolines produce different DNA cleavage patterns. For example, the 106 (C-T) cleavage observed with norindenoisoquinolines 5 and 15 is absent in 14d and 14e. Also, some of the cleavage sites induced with the norindenoisoquinolines appear to more closely resemble the indenoisoquinolines than the camptothecins. For example, the 44 (C-G) cleavage site is seen with the indenoisoquinoline MJ-III-65 and the norindenoisoquinolines 5,14a-e, and 15, but not with CPT, whereas the 37 (T-G) site is observed with CPT but not with the indenoisoquinolines and norindenoisoquinolines.

The DNA cleavage patterns induced by the norindenoisoquinolines may share some similarity with indenoisoquinolines, but distinguishing differences may also exist. For example, the 62 (C-A) site is observed with MJ-III-65 while

TABLE 3

Cytotoxicities of 14c against a series of selected human cancer cells (GI$_{50}$ in uM)

| | Leukemia | Non-small cell lung cancer | Melanoma | Ovarian Cancer | Prostate Cancer DU-145 | Breast Cancer | Colon Cancer | | Renal Cancer | | CNS Cancer | |
|---|---|---|---|---|---|---|---|---|---|---|---|---|
| | SR | NCI-H460 | UACC-62 | IGROVI | | MCF7 | HCC-2998 | COLO 205 | CAKI-1 | ACHN | U251 | SF-295 |
| 1$^{st}$ run | 0.012 | 0.16 | 0.21 | 0.033 | 0.26 | 0.09 | 0.11 | 0.76 | 0.17 | 0.27 | 0.15 | 0.16 |
| 2$^{nd}$ run | / | 0.11 | 0.18 | 0.21 | 0.41 | 0.089 | 2.1 | 0.28 | 0.40 | 0.30 | 0.17 | 0.13 |
| Mean | 0.012 | 0.13 | 0.20 | 0.12 | 0.33 | 0.090 | 1.1 | 0.51 | 0.29 | 0.28 | 0.16 | 0.15 |

Example

Norindenoisoquinolines 14a-f are examined for induction of Top1-mediated DNA cleavage using a 117-bp DNA oligonucleotide encompassing the previously identified Top1 cleavage sites in the 161-bp fragment from pBluescript SK(−) phagemid DNA (Dexheimer & Pommier DNA Cleavage Assay for the Identification of Topoisomerase I Inhibitors.

not with the norindenoisoquinolines. The 119 (T-G) site is found in the norindenoisoquinolines 14a-b but not with MJ-III-65. Introduction of W at C-10, appears to result in preferential binding to the 44 (C-G) site in comparison with the hydrophobic norindenoisoquinolines 5 and 15. The 97 (T-A) site observed in 5 and 15 is hardly detected in the norindenoisoquinolines 14a-e. Without being bound by theory, it is believed that these observations may be important because they may indicate that there could be selectivity in cancer gene targeting with the norindenoisoquinolines vs. indenoisoquinolines and CPT. It may be expected that different Top1 inhibitors may selectively target different tumor types.

Compound Examples

Melting points are determined in capillary tubes and are uncorrected. Infrared spectra are obtained using KBr pellets and are recorded using a Perkin-Elmer 1600 series FTIR. Except where noted, $^1$H NMR spectra are obtained using CDCl$_3$ as solvent and the solvent peak as internal standard. $^1$H NMR spectra are determined at 300 MHz on a Bruker ARX-300 spectrometer. Electrospray mass spectra are obtained using a Finnigan MATT LCQ (Thermoquest Corp., San Jose, Calif.). Microanalyses are performed at the Purdue University Microanalysis Laboratory. Chemicals and solvents are generally analytical grade and used without further purification, and purchased from commercial suppliers.

Example (3,4-Dimethoxybenzylidene)-(2,2-dimethoxyethyl) amine (7)

3,4-Dimethoxybenzaldehyde (12.20 g, 73.42 mmol) was dissolved in benzene (200 mL) and aminoacetaldehyde dimethyl acetal (12.0 mL, 11.7 g, 111 mmol) was added. The mixture was stirred at reflux for 4 h using a Dean-Stark trap. The reaction mixture was then concentrated and dissolved in CHCl$_3$ (250 mL). The solution was washed with water (4×150 mL) and brine (150 mL), dried (Na$_2$SO$_4$) and concentrated, and the last traces of solvent were removed under vacuum to provide the imine (18.41 g, 99.1%) as a light yellow solid: mp 50-52° C. $^1$H NMR (300 MHz, CDCl$_3$) δ 8.18 (s, 1H), 7.42 (s, 1H), 7.15 (d, J=8.4 Hz, 1H), 6.86 (d, J=8.4 Hz, 1H), 4.65 (t, J=5.1 Hz, 1H), 3.92 (s, 3H), 3.90 (s, 3H), 3.74 (d, J=5.1 Hz, 2H), 3.40 (s, 6H).

Example (3,4-Dimethoxybenzyl)-(2,2-dimethoxyethyl)amine (8)

The imine 7 (12.01 g, 47.47 mmol) was dissolved in ethanol (200 mL), and NaBH$_4$ (3.61 g, 95.4 mmol) was added over 0.5 h while the reaction mixture was stirred at reflux. The reaction mixture was diluted with water (200 mL). The amine was extracted into chloroform (250 mL) and the extract washed with water (2×150 mL) and brine (150 mL), dried (Na$_2$SO$_4$) and concentrated to provide clear colorless oil (10.65 g, 88%). $^1$H NMR (300 MHz, CDCl$_3$) δ 6.78-6.84 (m, 3H), 4.44 (t, J=5.4 Hz, 1H), 3.88 (s, 3H), 3.86 (s, 3H), 3.70 (s, 2H), 3.33 (s, 6H), 2.69 (d, J=5.4 Hz, 2H).

Example

2-Methylpiperonal (10)

n-BuLi (2.5 M in THF, 26.4 mL, 66 mmol) was added dropwise to a solution of N,N,N'-(trimethyl)ethylenediamine (8.6 mL, 6.79 g, 66.4 mmol) in THF (120 mL) at −78° C. (acetone-dry ice bath). After 15 min, piperonal (9.0 g, 60 mmol) was added, the mixture was stirred for 15 min, and n-BuLi (2.5 M in THF, 72 mL, 180 mmol) was added via syringe. After the reaction mixture was stirred for 1 h at −78° C., CH$_3$I (22.4 mL, 50.92 g, 360 mmol) was added at −78° C.

The mixture was stirred for 2 h at room temperature, poured into cold stirred 10% hydrochloric acid (prepared with 100 mL concentrated hydrochloric acid and 360 mL water), extracted with CHCl$_3$ (400 mL×3), washed with brine (400 mL), dried (Na$_2$SO$_4$), filtered and concentrated to give the crude product. Purification by preparative flash chromatography (SiO$_2$, EtOAc-hexane 10:1) gave the white crystalline product (6.71 g, 68.1%): mp 70-71° C. $^1$H NMR (300 MHz, CDCl$_3$) δ 9.96 (s, 1H), 7.34 (d, J=8.1 Hz, 1H), 6.78 (d, J=8.1 Hz, 1H), 6.04 (s, 2H), 2.50 (s, 3H).

Example (E)-2-Methylpiperonal O-Methyloxime (11)

2-Methyl-piperonal (10, 6.00 g, 36.5 mmol), O-methylhydroxyamine hydrochloride (6.11 g, 73.2 mmol) and sodium acetate hydrate (19.92 g, 146.4 mmol) were dissolved in methanol (200 mL) and the mixture was stirred at room temperature for 1 h. The reaction mixture was concentrated to dryness, ethyl acetate (200 mL) was added to the residue, and then 5% NaHCO$_3$ was added to neutralize acid. The solution was washed with brine (100 mL), dried (Na$_2$SO$_4$), filtered, and evaporated under vacuum to afford 11 (5.92 g, 84%) as a solid: mp 34° C. IR (KBr) 2894, 1642, 1598, 1458, 1343, 1270, 1055 cm$^{-1}$; $^1$H NMR (300 MHz, CDCl$_3$) δ 8.18 (s, 1H), 7.17 (d, J=8.1 Hz, 1H), 6.66 (d, J=8.1 Hz, 1H), 5.96 (s, 2H), 3.93 (s, 3H), 2.28 (s, 3H); low resolution ESIMS m/z (rel intensity) 194 (MH$^+$, 100). Anal. (C$_{10}$H$_{11}$NO$_3$) C, H, N.

Example (E)-2-Bromomethylpiperonal O-Methyloxime (12)

A solution of the oxime 11 (4.00 g, 20.7 mmol), NBS (4.43 g, 2.49 mmol), AIBN (0.4078 g, 2.49 mmol) in carbon tetrachloride (100 mL) was stirred at reflux under argon for 3 h. The reaction mixture was cooled to room temperature, filtered and evaporated to give the crude product 12. Purification by preparative flash chromatography (SiO$_2$, EtOAc-hexane 15:1) and then recrystallization from hexane gave the final pure product (3.27 g, 58%) as a white solid: mp 122-123° C. IR (KBr) 2902, 1480, 1455, 1265, 1048, 927 cm$^{-1}$; $^1$H NMR (300 MHz, CDCl$_3$) δ 8.19 (s, 1H), 7.09 (d, J=8.1 Hz, 1H), 6.75 (d, J=8.1 Hz, 1H), 6.05 (s, 2H), 4.73 (s, 2H), 3.97 (s, 3H); low resolution ESIMS m/z (rel intensity) 272 (MH$^+$, 37), 192 [(M−Br)$^+$, 100]. Anal. (C$_{10}$H$_{10}$BrNO$_3$) C, H, N.

Example (E)-4-[(Dimethylamino)methyl]benzo[d][1,3]diox-ole-5-carbaldehyde O-Methyl Oxime (13a)

A solution of the oxime 12 (0.40 g, 1.47 mmol) in THF (10 mL) was added by syringe during 15 min to dimethylamine (2 M in THF, 3 mL, 6 mmol) at 0° C. The reaction mixture was stirred at room temperature for 2 h. The organic solvent was removed by evaporation under reduced pressure. A 5% NaHCO$_3$ aqueous solution (20 mL) was added to the residue, which was further extracted with EtOAc (40 mL×2). The organic layer was washed with brine (5 mL) and dried (Na$_2$SO$_4$). Filtration and evaporation under reduced pressure gave 13a as a yellow oil (0.3122 g, 90%). IR (KBr) 2939, 1474, 1455, 1253, 1053 cm$^{-1}$; $^1$H NMR δ (300 MHz, CDCl$_3$) 8.39 (s, 1H), 7.33 (d, J=8.1 Hz, 1H), 6.73 (d, J=8.1 Hz, 1H), 5.96 (s, 2H), 3.93 (s, 3H), 3.47 (s, 2H), 2.22 (s, 6H); low resolution ESIMS m/z (rel intensity) 237 (MH⁺, 100), 192 [(M–NHMe₂)⁺, 55]. Anal. ($C_{12}H_{16}N_2O_3$) C, H, N.

Example (E)-4-(Pyrrolidin-1-ylmethyl)benzo[d][1,3]dioxole-5-carbaldehyde O-Methyl Oxime (13b)

A solution of the oxime 12 (0.95 g, 3.49 mmol) in THF (10 mL) was added by syringe to a solution of pyrrolidine (0.72 mL, 0.62 g, 8.7 mmol) in THF (10 mL) at 0° C. The reaction mixture was stirred at room temperature for 2 h. The organic solvent was removed by evaporation under reduced pressure. An aqueous solution of 5% NaHCO₃ (20 mL) was added to the residue, and the mixture was extracted with EtOAc (40 mL×2). The organic layer was washed with brine (20 mL) and dried (Na₂SO₄). Filtration and evaporation under reduced pressure gave 13b as a yellow oil (0.801 g, 88%). IR (KBr) 2960, 1473, 1455, 1253, 1051 cm⁻¹, ¹H NMR (300 MHz, CDCl₃) δ 8.48 (s, 1H), 7.35 (d, J=8.1 Hz, 1H), 6.74 (d, J=8.1 Hz, 1H), 5.97 (s, 2H), 3.95 (s, 3H), 3.70 (s, 2H), 2.54 (broad s, 4H), 1.72 (broad s, 4H); ESIMS m/z (rel intensity) 263 (MH⁺, 100). Anal. ($C_{14}H_{18}N_2O_3$) C, H, N.

Example (E)-4-[(1H-Imidazol-1-yl)methyl]benzo[d][1,3]dioxole-5-carbaldehyde O-Methyl Oxime (13c)

A THF solution (3 mL) of the oxime 12 (0.40 g, 1.47 mmol) was added by syringe during 15 min to a solution of imidazole (0.40 g, 5.88 mmol) in THF (10 mL) at 0° C. The reaction mixture was stirred at room temperature for 2 h. The organic solvent was removed by evaporation under reduced pressure. An aqueous 5% NaHCO₃ solution (10 mL) was added to the residue, and the mixture was extracted with EtOAc (40 mL×2). The organic layer was washed with brine (20 mL) and dried (Na₂SO₄). Filtration and evaporation under reduced pressure gave 13c as a yellow solid (0.32 g, 84%): mp 102° C. IR (KBr) 2964, 1462, 1271, 1051 cm⁻¹, ¹H NMR (300 MHz, CDCl₃) δ 8.06 (s, 1H), 7.63 (s, 1H), 7.03 (brs, 1H), 6.97 (brs, 1H), 6.90 (d, J=8.1 Hz, 1H), 6.78 (d, J=8.1 Hz, 1H), 6.04 (s, 2H), 5.43 (s, 2H), 3.96 (s, 3H); ESIMS m/z (rel intensity) 260 (MH⁺, 100). Anal. ($C_{13}H_{13}N_3O_3$) C, H, N.

Example

4-[(4-Methylpiperazin-1-yl)methyl]benzo[d][1,3]dioxole-5-carbaldehyde O-Methyl Oxime (13d)

A solution of the oxime 12 (360.0 mg, 1.324 mmol) in THF (10 mL) was added by syringe during 30 min to a solution of 4-methylpiperazine (400.0 mg, 4.00 mmol) in THF (10 mL) at 0° C. The reaction mixture was then stirred at room temperature for 4 h. The organic solvent was removed by evaporation under reduced pressure. An aqueous 5% NaHCO₃ solution (20 mL) was added to the residue, and the mixture was extracted with EtOAc (40 mL×2). The organic layer was washed with brine (20 mL) and dried (Na₂SO₄). Filtration and evaporation under reduced pressure gave 13d as a yellow solid (303.1 mg, 78%): mp 100-102° C. IR 2937, 1473, 1455, 1295, 1050 cm⁻¹; ¹H NMR (300 MHz, CDCl₃) δ 8.47 (s, 1H), 7.39 (d, J=8.2 Hz, 1H), 6.74 (d, J=8.2 Hz, 1H), 5.97 (s, 2H), 3.96 (s, 3H), 3.96 (s, 2H), 3.53 (s, 3H), 2.46 (brs, 8H), 2.26 (s, 3H); ESIMS m/z (rel intensity) 292 (MH⁺, 100), 192 (10).

Example 4-(Morpholinomethyl)benzo[d][1,3]dioxole-5-carbaldehyde O-Methyl Oxime (13e)

A solution of the oxime 12 (400.0 mg, 1.47 mmol) in THF (10 mL) was added by syringe during 30 min to a solution of morpholine (510.0 mg, 5.86 mmol) in THF (10 mL) at 0° C. The reaction mixture was stirred at room temperature for 2 h. The organic solvent was removed by evaporation under reduced pressure. An aqueous 5% NaHCO₃ solution (20 mL) was added to the residue, and the mixture was extracted with EtOAc (40 mL×2). The organic layer was washed with brine (20 mL) and dried (Na₂SO₄). Filtration and evaporation under reduced pressure gave 13e as a yellow oil (369.0 mg, 90.2%): IR 2896, 1473, 1455, 1254, 1050 cm⁻¹; ¹H NMR (300 MHz, CDCl₃) δ 8.46 (s, 1H), 7.38 (d, J=8.4 Hz, 1H), 6.74 (d, J=8.4 Hz, 1H), 5.98 (s, 2H), 3.95 (s, 3H), 3.67 (t, J=4.6 Hz, 4H), 3.53 (s, 2H), 2.44 (t, J=4.6 Hz, 4H); ESIMS m/z (rel intensity) 279 (MH⁺, 100), 192 (30).

Example 4-(((2-(Dimethylamino)ethyl)(methyl)amino)methyl)-benzo[d][1,3]dioxole-5-carbaldehyde O-Methyl Oxime (13f)

A solution of the oxime 12 (908.1 mg, 3.34 mmol) in THF (10 mL) was added by syringe during 15 min to N,N,N'-trimethylethylenediamine (1021.2 mg, 9.994 mmol) in THF (5 mL) at 0° C. The reaction mixture was stirred at room temperature for 4 h. The organic solvent was removed by evaporation under reduced pressure. An aqueous 5% NaHCO₃ solution (10 mL) was added to the residue, which was further extracted with EtOAc (20 mL×2). The organic layer was washed with brine (10 mL) and dried (Na₂SO₄). Filtration and evaporation under reduced pressure gave 13f as a yellow oil (485.2 mg, 49.4%): IR 2939, 1473, 1455, 1254, 1051 cm⁻¹; ¹H NMR (300 MHz, CDCl₃) δ 8.51 (s, 1H), 7.37 (d, J=8.1 Hz, 1H), 6.73 (d, J=8.1 Hz, 1H), 5.97 (s, 2H), 3.94 (s, 3H), 3.59 (s, 3H), 2.52 (t, J=6.5 Hz, 2H), 2.43 (t, J=6.5 Hz, 2H), 2.21 (s, 9H); ESIMS m/z (rel intensity) 294 (MH⁺, 100), 249 [(M-Me₂NH)⁺, 80].

Example 2,3-Dimethoxy-8,9-methylenedioxy-10-(dimethylamino)methyl-11H-indeno[1,2-c]isoquinoline (14a)

The amine 8 (0.30 g, 1.18 mmol) and oxime ether 13a (0.126 g, 0.534 mmol) were mixed with concentrated hydrochloric acid (7 mL) and the mixture was stirred at 100° C. for 18 h. The reaction mixture was cooled and washed with ether (3×20 mL). It was then brought to basic pH with NH₄OH. The mixture was extracted with chloroform (40 mL×3) and the solution was washed with brine (50 mL), dried (Na₂SO₄) and concentrated. The residue was diluted in chloroform (40 mL) and filtered. Hydrochloric acid (2 M HCl in ether, 5 mL) was added to the filtrate. The precipitate that formed was recrystallized from methanol to provide a yellow solid. The solid was dissolved in water, basified with NH₄OH and extracted with chloroform. The organic layer was concentrated to dryness. The residue was purified by preparative flash chromatography (SiO₂, methanol-chloroform-TEA=3:97:2) to afford the final product 14a as a light yellow solid (0.0162 g, 7.8%): mp 205-207° C. IR (KBr) 2940, 1449, 1408, 1326, 1246, 1159, 1061 cm⁻¹; ¹H NMR (300 MHz, CDCl₃) δ 8.98

(s, 1H), 7.62 (s, 1H), 7.23 (s, 1H), 7.16 (s, 1H), 6.11 (s, 2H), 4.21 (s, 2H), 4.10 (s, 3 H), 4.05 (s, 3H), 2.77 (s, 6H); low resolution ESIMS m/z (rel intensity) 379 (MH$^+$, 100), 334 (90). Anal. ($C_{22}H_{22}N_2O_4 \cdot 1.25H_2O$) C, H, N.

Example 2,3-Dimethoxy-8,9-methylenedioxy-10-(pyrrolidin-1-yl)methyl-11H-indeno[1,2-c]isoquinoline (14b)

The amine 8 (1.90 g, 7.45 mmol) and oxime ether 13b (0.90 g, 3.44 mmol) were mixed with concentrated hydrochloric acid (15 mL) and the mixture was stirred at 100° C. for 18 h. The reaction mixture was then cooled and washed with ether (3×20 mL). It was then brought to basic pH with NH$_4$OH. The mixture was extracted with chloroform (40 mL×3), and the solution was washed with brine (50 mL), dried (Na$_2$SO$_4$) and concentrated. The residue was dissolved in chloroform (40 mL) and filtered. Hydrochloric acid (2 M HCl in ether, 5 mL) was added to the filtrate. The precipitate that formed was recrystallized from methanol to provide a yellow solid. The solid was dissolved in water, basified with NH$_4$OH and extracted with chloroform. The organic layer was concentrated to dryness. The residue was purified by preparative flash chromatography (SiO$_2$, methanol-chloroform-TEA=3:97:2) to yield the final pure product 14b as a light yellow solid (84.9 mg, 6.1%): mp 210° C. (dec). IR (KBr) 2958, 1449, 1406, 1326, 1246 cm$^{-1}$; $^1$H NMR (300 MHz, CDCl$_3$) δ 8.94 (s, 1H), 7.44 (s, 1H), 7.16 (s, 1H), 7.01 (s, 1H), 6.04 (s, 2H), 4.07 (s, 3H), 4.02 (s, 3H), 3.85 (s, 2H), 3.79 (s, 2H), 2.67 (broad s, 4H), 1.82 (broad s, 4H); low resolution ESIMS m/z (rel intensity) 405 (MH$^+$, 15), 334 (100). Anal. ($C_{24}H_{24}N_2O_4 \cdot 1.75H_2O$) C, H, N.

Example 2,3-Dimethoxy-8,9-methylenedioxy-10-(1H-imidazol-yl)methyl-11H-indeno[1,2-c]isoquinoline (14c)

The amine 8 (0.905 g, 3.55 mmol) and oxime ether 13c (0.41 g, 1.6 mmol) were mixed with concentrated hydrochloric acid (8 mL) and the mixture was stirred at 100° C. for 18 h. The reaction mixture was then cooled and washed with ether (3×20 mL). It was then brought to basic pH with NH$_4$OH. The mixture was extracted with chloroform (40 mL×3), and the solution was washed with brine (50 mL), dried (Na$_2$SO$_4$) and concentrated. The residue was diluted in chloroform (40 mL) and filtered. Hydrochloric acid (2 M HCl in ether, 5 mL) was added to the filtrate. The precipitate that formed was recrystallized from methanol to provide a yellow solid. The solid was dissolved in water, basified with NH$_4$OH and extracted with chloroform. The organic layer was concentrated to dryness. The residue was purified by preparative flash chromatography (SiO$_2$, methanol-chloroform-TEA=10:90:2) to afford the final pure product 14c as a light brown solid (0.0419 g, 6.6%): mp 250° C. (dec). IR (KBr) 2961, 1496, 1413, 1207, 1020 cm$^{-1}$; $^1$H NMR (300 MHz, DMSO) δ 9.01 (s, 1H), 7.84 (s, 1H), 7.54 (s, 1H), 7.39 (s, 1H), 7.31 (s, 1H), 7.24 (s, 1H), 6.90 (s, 1H), 6.15 (s, 2H), 5.33 (s, 2H), 4.08 (s, 3H), 3.99 (s, 3H), 3.92 (s, 3H); low resolution ESIMS m/z (rel intensity) 402 (MH$^+$, 100), 334 (15). Anal. ($C_{23}H_{19}N_3O_4 \cdot 1.5H_2O$) C, H, N.

Example 2,3-Dimethoxy-8,9-methylenedioxy-10-(4-methylpiperazin-1-yl)methyl-11H-indeno[1,2-c]isoquinoline (14d)

The amine 8 (560.3 mg, 2.19 mmol) and oxime ether 13d (320.2 mg, 1.10 mmol) were mixed together with concentrated hydrochloric acid (10 mL) and the mixture was stirred at 100° C. for 3 h. The reaction mixture was then cooled and washed with ether (3×20 mL). It was then brought to basic pH with 28% aqueous NH$_4$OH. The mixture was extracted with CHCl$_3$ (3×40 mL), and the organic layer was washed with brine (50 mL), dried with anhydrous Na$_2$SO$_4$ and concentrated. The residue was diluted in CHCl$_3$ (40 mL) and filtered. Hydrochloric acid (2 M HCl in ether, 10 mL) was added to the filtrate. A dark yellow precipitate was obtained and recrystallized from methanol to provide a bright yellow solid. NH$_4$OH (2 mL) was added to the yellow solid and the mixture was concentrated to dryness. The residue was purified by preparative flash chromatography (SiO$_2$, methanol-chloroform-TEA=10:90:2) to yield the final pure product 14d as a yellow solid (16.7 mg, 3.5%): mp 296° C. (dec). IR 3400, 1489, 1455, 1245, 1159 cm$^{-1}$; $^1$H NMR (300 MHz, CDCl$_3$) δ 8.98 (s, 1H), 7.47 (s, 1H), 7.24 (s, 1H), 7.08 (s, 1H), 6.04 (s, 2H), 4.11 (s, 3H), 4.04 (s, 3H), 3.91 (s, 2H), 3.68 (s, 2H), 2.65 (brs, 4H), 2.56 (brs, 4H), 2.34 (s, 3H); ESIMS m/z (rel intensity) 434 (MH$^+$, 100), 334 (25). Anal. ($C_{25}H_{27}N_3O_4 \cdot 3.5H_2O$) C, H, N.

Example 2,3-Dimethoxy-8,9-methylenedioxy-10-(4-morpholino)methyl-11H-indeno[1,2-c]isoquinoline (14e)

The amine 8 (660.0 mg, 2.59 mmol) and oxime 13e (320.0 mg, 1.15 mmol) were mixed together with concentrated hydrochloric acid (10 mL) and stirred at 100° C. for 3 h. The reaction mixture was cooled and washed with ether (3×20 mL). It was brought to basic pH with 28% aqueous NH$_4$OH. The mixture was extracted with CHCl$_3$ (3×40 mL), and the organic layer was washed with brine (50 mL), dried with anhydrous Na$_2$SO$_4$ and concentrated. The residue was diluted in CHCl$_3$ (40 mL) and filtered. Hydrochloric acid (2 M HCl in ether, 10 mL) was added to the filtrate. A dark yellow precipitate was obtained and then recrystallized from methanol to provide a bright yellow solid. NH$_4$OH (2 mL) was added to the yellow solid and the mixture was extracted with CHCl$_3$ (3×20 mL) and concentrated to dryness. The residue was purified by preparative flash chromatography (SiO$_2$, methanol-chloroform-TEA=5:95:2) to afford the final pure product as a golden crystalline solid 14e (32.2 mg, 6.7%): mp 269° C. (dec). IR 3400, 1489, 1455, 1249, 1115 cm$^{-1}$; $^1$H NMR (300 MHz, CDCl$_3$) δ 8.99 (s, 1H), 7.49 (s, 1H), 7.11 (s, 1H), 6.04 (s, 2H), 4.12 (s, 3H), 4.05 (s, 3H), 3.97 (s, 2H), 3.72 (t, J=4.5 Hz, 4H), 3.68 (s, 2H), 2.56 (t, J=4.5 Hz, 4H); ESIMS m/z (rel intensity) 421 (MH$^+$, 100), 334 (32). Anal. ($C_{24}H_{24}N_2O_5 \cdot 0.4H_2O$) C, H, N.

Example 2,3-Dimethoxy-8,9-methylenedioxy-10-(N,N,N'-trimethylethylenediamino)methyl-11H-indeno[1,2-c]isoquinoline (14f)

The amine 8 (1020 mg, 4.00 mmol) and oxime ether 13f (458.1 mg, 1.56 mmol) were mixed together with concentrated hydrochloric acid (10 mL) and the mixture was stirred at 100° C. for 18 h. The reaction mixture was cooled and washed with ether (3×20 mL). It was then brought to basic pH with NaOH (10% aqueous) at 0° C. (water-ice bath). The mixture was extracted with CHCl$_3$ (3×40 mL), and the organic layer was washed with brine (50 mL), dried with anhydrous Na$_2$SO$_4$ and concentrated. The residue was diluted in CHCl$_3$ (40 mL) and filtered. Hydrochloric acid (2M HCl in ether, 10 mL) was added to the filtrate. The dark yellow precipitate was recrystallized from methanol to provide a bright yellow solid. NH$_4$OH (2 mL) was added to the yellow solid and the mixture was concentrated to dryness. The residue was purified by preparative flash chromatography (SiO$_2$, methanol-chloroform-TEA=10:90:2) to provide the final pure product as a yellow solid 14f (21.1 mg, 3.1%): mp 192° C. IR 3400, 2944, 1488, 1247, 1060 cm$^{-1}$; $^1$H NMR (300 MHz, CDCl$_3$) δ 8.95 (s, 1H), 7.45 (s, 1H), 7.20 (s, 1H), 7.04 (s, 1H), 6.03 (s, 2H), 4.09 (s, 3H), 3.91 (s, 3H), 3.84 (s, 2H), 3.62 (s, 2H), 2.58 (t, J=6.3 Hz, 2H), 2.50 (t, J=6.3 Hz, 2H), 2.29 (s, 3H), 2.22 (s, 6H): ESIMS m/z (rel intensity) 436 (MH$^+$, 85), 391 (MH$^+$-Me$_2$NH, 22), 334 (MH$^+$—CH$_3$NHCH$_2$CH$_2$N(CH$_3$)$_2$, 100); HRESIMS calculated 435.2236. found 436.2240 (MH$^+$); purity 98.6% (HPLC).

Example 2,3-Dimethoxy-8,9-methylenedioxy-10-methyl-11H-indeno[1,2-c]isoquinoline (15)

The amine 8 (0.640 g, 2.51 mmol) and 2-methylpiperonal (10, 0.450 g, 2.74 mmol) were mixed with concentrated hydrochloric acid (8 mL) and the mixture was stirred at 100° C. for 18 h. The reaction mixture was then cooled and washed with ether (3×20 mL). It was then brought to basic pH with NH$_4$OH. The mixture was extracted with chloroform (40 mL×3), and the solution was washed with brine (50 mL), dried (Na$_2$SO$_4$) and concentrated. The residue was dissolved in chloroform (40 mL) and filtered. Hydrochloric acid (2 M HCl in ether, 8.7 mL) was added to the filtrate. The precipitate that formed was recrystallized from methanol to provide a yellow solid. The solid was dissolved in water, basified with NH$_4$OH and extracted with chloroform. The organic layer was concentrated to dryness. The residue was purified by preparative flash chromatography (SiO$_2$, acetone-chloroform-TEA=20:80:2) to afford the final pure product as a light yellow solid (0.025 g, 3.0%): mp 272-274° C. (dec). IR (KBr) 2902, 1487, 1240, 1075 cm$^{-1}$; $^1$H NMR (300 MHz, CDCl$_3$) δ 8.96 (s, 1H), 7.41 (s, 1H), 7.22 (s, 1H), 7.21 (s, 1H), 6.02 (s, 2H), 4.07 (s, 3H), 4.02 (s, 3H), 3.78 (s, 2H), 2.33 (s, 3H); low resolution ESIMS m/z (rel intensity) 336 (MH$^+$, 100). Anal. (C$_{20}$H$_{17}$NO$_4$·0.5H$_2$O) C, H, N.

Example

Topoisomerase I-Mediated DNA Cleavage Reactions

Human recombinant Top1 was purified from baculovirus as previously described.[46] DNA cleavage reactions were prepared as previously reported with the exception of the DNA substrate.[13] Briefly, a 117-bp DNA oligonucleotide (Integrated DNA Technologies) encompassing the previously identified Top1 cleavage sites in the 161-bp fragment from pBluescript SK(−) phagemid DNA was employed. This 117-bp oligonucleotide contains a single 5'-cytosine overhang, which was 3'-end labeled by fill-in reaction with [α-$^{32}$P]-dGTP in React 2 buffer (50 mM Tris-HCl, pH 8.0, 100 mM MgCl$_2$, 50 mM NaCl) with 0.5 units of DNA polymerase I (Klenow fragment, New England BioLabs). Unincorporated $^{32}$P-dGTP was removed using mini Quick Spin DNA columns (Roche, Indianapolis, Ind.), and the eluate containing the 3'-end-labeled DNA substrate was collected. Approximately 2 nM of radiolabeled DNA substrate was incubated with recombinant Top1 in 20 μL of reaction buffer [10 mM Tris-HCl (pH 7.5), 50 mM KCl, 5 mM MgCl$_2$, 0.1 mM EDTA, and 15 μg/ml BSA] at 25° C. for 20 min in the presence of various concentrations of compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromphenol blue). Aliquots of each reaction were subjected to 20% denaturing PAGE. Gels were dried and visualized by using a Phosphoimager and ImageQuant software (Molecular Dynamics). For simplicity, cleavage sites were numbered as previously described in the 161-bp fragment.

COMPUTATION EXAMPLES

Example

Acid-Base Dissociation Constants

The pK$_a$ values of the amines 14a-f were calculated to determine the dominant species at physiological pH 7.4 using the on-line program ADME Boxes (http://www.pharma-algorithms.com/webboxes/) from Pharma Algorithms (Balogh et al., Comparative Evaluation of in Silico pKa Prediction Tools on the Gold Standard Dataset. *QSAR Comb. Sci.* 1009, 28, 1148-1155). The method employs the pKa prediction tool of Pharma Algorithms used herein. The algorithm utilizes ca. 18000 experimental pKa data points, a database of ca. 4600 ionization centers, ca. 500 interaction constants and four interaction calculation methods to produce microconstants. In addition, the Log P and Log D values were also calculated with the Pharma Algorithms on-line service. The data suggest that the introduction of W at C-10 decreases the Log D values of the compounds compared to the parent. It is appreciated that the aqueous solubilities of the compounds described herein, including 14a-f, may be further increased through salt formation.

The data may indicate that 14a and 14b against Top1 have tertiary amines with pK$_a$ values of about 8.6. This pK$_a$ value indicates that the nitrogen atom attached to 10-benzyl group of norindenoisoquinoline may be 95% protonated at physiological pH. The dominant species of 14d and 14f are monoprotonated on their distal nitrogens. For compounds containing two nitrogen atoms such as piperazine, one nitrogen atom may be protonated first, making the other nitrogen less basic. For example, the pK$_a$ values of piperazine are 9.81 and 5.59, respectively (Boyd & Paull, Some Practical Considerations and Applications of the National Cancer Institute In Vitro Anticancer Drug Discovery Screen. *Drug Development Res.* 1995, 34, 91-109). As for 14c and 14e, the dominant species may be unprotonated forms (88% and 95%, respectively) at physiological pH.

Example

X-Ray Crystal Structure

The crystal structure (FIG. 1) of the norindenoisoquinoline 14a was determined and may be used as a starting conformation for the quantum chemical calculations. It has been observed that one crystal form of compound 14a is a co-crystal with chloroform, thus forming a solvate as described herein.

Example

Molecular Docking

To further explore the influence of protonation states of 14a and 14b on Top1 inhibition, the protonated form and also the free bases of these two compounds were docked into Top1-DNA covalent complex (PDB: 1t18). Norindenoisoquinoline 14b was built based on the crystal structure of 14a in SYBYL 8.0.3 software from Tripos. The protonated form of 14b was further built by modifying the atom type of the pyrrolidine nitrogen atom from N3 to N4 and then adding hydrogen atoms. Both molecules were minimized using the MMFF94s force field, MMFF94 charges, and the conjugate gradient method, with simplex initial optimization, to a gradient of less than 0.001 kcal/mol. The conformations are docked to Top1-DNA complex (PDB: 1t18) by CCDC's molecular docking software GOLD[49] 3.0.1 using default settings. The binding region is defined as all the atoms that are 12 Å around the centroid of norindenoisoquinoline 5 in the crystal structure. Early termination is allowed if the top three solutions are within 1.5 Å rms deviation. To rank docking results, the GoldScore fitness scores are used. The top three energy-ranked structures for each ligand are saved for graphic analysis. The resulting complexes are further minimized using MMFF94s force field, MMFF94 charges as above. The binding energies are calculated by the equation shown below:

$$E_{binding} = E_{complex} - E_{protein} - E_{ligand}.$$

It appears that the protonated species may form stronger interactions with the Top1-DNA covalent complex compared to the free bases. For example, the hydrogen atom from protonation attached to the pyrrolidine nitrogen atom may form a direct hydrogen bond with Glu356 of Top1. Moreover, the isoquinoline nitrogen atom at the 6-position of the norindenoisoquinoline may form a characteristic hydrogen bond with Arg364 and one oxygen atom of the methylenedioxy group neighboring the 10-position of norindenoisoquinoline forms a hydrogen bond with Lys425.

In contrast, without being bound by theory, it is believed herein that the most potent compound 14c may exist predominantly in its neutral form (88%) at physiological pH based on calculated pKa values. From molecular docking studies, the neutral form appears to afford a less favorable binding energy (−71.7130 kcal/mol) than the other nitrogen-containing sidechain substituted norindenoisoquinolines.

Example

Quantum Chemistry Calculation

The DNA-binding energies of 14a and 15 to the simplified DNA cleavage site of Top1, and the solvation energies, are calculated using published methods and strategies (Song & Cushman, The Binding Orientation of a Norindenoisoquinoline in the Topoisomerase I-DNA Cleavage Complex Is Primarily Foverned by pi-pi Stacking Interactions. *J. Phys. Chem. B* 2008, 112, 9484-9489). The molecules are built starting from the crystal structure of 14a in SYBYL and geometry optimizations and frequency calculations are carried out for each compound at the HF/6-31G** level. The energy-minimized structures display no imaginary frequencies and are therefore utilized to replace the original ligand in the simplified DNA model. The model is then subjected to single-point energy calculations using the MP2 method at the modified 6-31G*(0.25) level using the quantum chemical program package Gaussian 03. The effect of solvation is investigated using the Polarizable Continuum Model (PCM) at the MP2/6-31G*(0.25) level with the default radii scheme.

The intermolecular interaction energy is calculated using the supermolecular approach (Table 1). The energy of interaction between the ligand and the neighboring DNA base pairs is defined as the difference between the energy of the complex $E_{complex}$ and the energies of the monomers $E_{ligand}$ and $E_{bp}$. The basis set superposition error (BSSE) is also corrected using the Boys and Bernardi counterpoise method because of the use of an incomplete basis set in practical applications of the supermolecular approach. Therefore, the interaction energies of the two compounds 14a and 15 are calculated at the MP2/6-31G*(0.25) level through the equation listed below:

$$E_{int} = E_{complex} - E_{ligand} - E_{bp} + BSSE$$

TABLE 1

Interaction and Solvation Energies (kcal/mol) of Norindenoisoquinolines Binding to Simplified Cleavage Complex[37] Calculated by the MP2/6-31G * (0.25) Method

| | Compound | | |
|---|---|---|---|
| Parameters | 5 | 15 | 14a[d] |
| $E_{int}$ (MP2)[a] | −31.56 | −32.87 | −31.77* |
| $\Delta G_{solvation}$ (MP2)[b] | −40.25 | −38.32 | −36.53* |
| $E_{int} + \Delta G_{solvation}$ | −71.81 | −71.19 | −68.3* |
| $\Delta E^c$ | 0 | 0.62 | 3.51* |

[a]$E_{int} = E_{complex} - E_{ligand} - E_{bp} + BSSE$
[b]$\Delta G_{solvation}$ (MP2) = $E_{PCM-MP2} - E_{MP2}$
[c]$\Delta E$ was the relative binding energy difference in aqueous solution between 15, 14a and AI-III-52 investigated at the MP2 level, respectively.
[d]The 10-position substituent of 14a forms direct interactions with neighboring Top1 residues which were not included in the MP2 calculations due to impractically high computational cost. Therefore, the values with an asterisk may not be meaningful indicators of binding to the DNA-Top1 covalent complex.

What is claimed is:
1. A process for preparing a compound of the formula

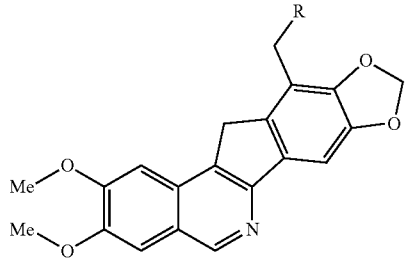

or a pharmaceutically acceptable salt thereof,
wherein
R is dimethylamino, pyrrolidin-1-yl, 1H-imidazolyl, 4-methylpiperazin-1-yl, 4-morpholino, or N,N,N'-trimethylethylenediamino;
the process comprising the step of treating a compound of formula

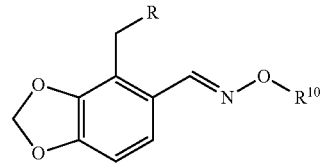

with a compound of formula

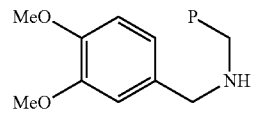

and an acid; wherein
$R^{10}$ is alkyl; and
P is an aldehyde or protected acetal.

2. The process of claim 1, wherein said acid is HCl.

3. A compound of the formula

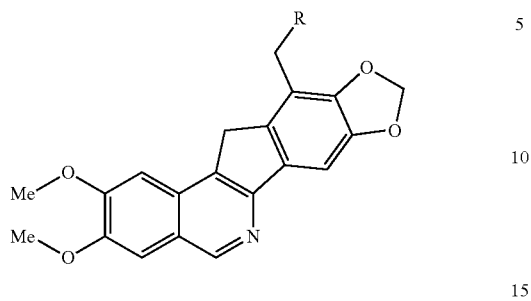

or a pharmaceutically acceptable salt thereof, wherein
R is dimethylamino, pyrrolidin-1-yl, 1H-imidazolyl, 4-methylpiperazin-1-yl, 4-morpholino, or N,N,N'-trimethylethylenediamino.

4. The compound of claim 3, wherein R is 1H-imidazolyl.

5. A composition comprising one or more compounds of claim 3, and optionally one or more carriers, diluents, or excipients, or a combination thereof.

6. A method for inhibiting topoisomerase 1, the method comprising the step of contacting topoisomerase 1 with an effective amount of one or more compounds of claim 3.

* * * * *